(12) United States Patent
Old et al.

(10) Patent No.: US 9,131,842 B2
(45) Date of Patent: Sep. 15, 2015

(54) SYSTEM AND METHODS FOR LOCATING RELATIVE POSITIONS OF MULTIPLE PATIENT ANTENNAS

(71) Applicant: Rock West Solutions, Inc., San Diego, CA (US)

(72) Inventors: Thomas Eugene Old, Santa Barbara, CA (US); John Christopher Baker, Santa Barbara, CA (US); Neal J. Carron, Goleta, CA (US); Donald Gordon Pritchett, Santa Barbara, CA (US)

(73) Assignee: Rock West Solutions, Inc., San Diego, CA (US)

( * ) Notice: Subject to any disclaimer, the term of this patent is extended or adjusted under 35 U.S.C. 154(b) by 0 days.

(21) Appl. No.: 13/969,423

(22) Filed: Aug. 16, 2013

(65) Prior Publication Data

US 2014/0051949 A1 Feb. 20, 2014

Related U.S. Application Data

(60) Provisional application No. 61/683,851, filed on Aug. 16, 2012, provisional application No. 61/784,340, filed on Mar. 14, 2013.

(51) Int. Cl.
*A61B 5/07* (2006.01)
*A61B 5/00* (2006.01)
(Continued)

(52) U.S. Cl.
CPC ............. *A61B 5/0002* (2013.01); *A61B 5/061* (2013.01); *A61B 5/073* (2013.01); *A61B 1/041* (2013.01); *A61B 5/062* (2013.01); *A61B 2019/5251* (2013.01); *A61B 2019/5272* (2013.01);
(Continued)

(58) Field of Classification Search
USPC .................................. 600/424, 428
See application file for complete search history.

(56) References Cited

U.S. PATENT DOCUMENTS 5,279,607 A 1/1994 Schentag et al.
6,498,477 B1 * 12/2002 Govari et al. ............ 324/207.12
(Continued)

FOREIGN PATENT DOCUMENTS

CN 200984246 12/2007
CN 101108122 A 1/2008
(Continued)

OTHER PUBLICATIONS

International Search Report and Written Opinion in PCT/US2013/055461 dated Oct. 23, 2013 in 11 pages.
(Continued)

*Primary Examiner* — Michael Kahelin
*Assistant Examiner* — Mitchell E Alter
(74) *Attorney, Agent, or Firm* — Knobbe Martens Olson & Bear LLP

(57) ABSTRACT

Systems and methods described herein use near field communications to locate a set of antennas attached to, coupled with, or near the patient. A signal emitted by an antenna in the set of antennas can be received by the other antennas in the set. A second signal can be further transmitted from another antenna in the set. The differential phase and/or time shifts between the antennas from the multiple signal transmissions can contain sufficient information to find the locations of the antennas in antenna centric coordinates. The antenna locations can then be used to find a location of a pill transmitter swallowed by the patient.

18 Claims, 17 Drawing Sheets

(51) Int. Cl.
*A61B 5/06* (2006.01)
*A61B 1/04* (2006.01)
*A61B 19/00* (2006.01)
*G01S 5/02* (2010.01)
*G01S 11/06* (2006.01)

(52) U.S. Cl.
CPC ............ *G01S5/0289* (2013.01); *G01S 5/0294* (2013.01); *G01S 11/06* (2013.01)

(56) References Cited

U.S. PATENT DOCUMENTS

| | | |
|---|---|---|
| 6,929,636 B1 | 8/2005 | von Alten |
| 6,950,690 B1 | 9/2005 | Meron et al. |
| 7,109,933 B2 | 9/2006 | Ito et al. |
| 7,359,765 B2 | 4/2008 | Varvarelis et al. |
| 7,382,263 B2 | 6/2008 | Danowski et al. |
| 7,596,403 B2 | 9/2009 | Horn |
| 7,761,134 B2 | 7/2010 | Horn et al. |
| 7,796,043 B2 | 9/2010 | Euliano et al. |
| 7,797,033 B2 | 9/2010 | D'Andrea et al. |
| 7,822,463 B2 | 10/2010 | Meron et al. |
| 8,052,595 B2 | 11/2011 | Minai |
| 8,147,482 B2 | 4/2012 | Shimizu et al. |
| 8,512,241 B2 | 8/2013 | Bandy et al. |
| 8,518,022 B2 | 8/2013 | Trovato et al. |
| 8,597,278 B2 | 12/2013 | Trovato et al. |
| 8,597,279 B2 | 12/2013 | Dijksman et al. |
| 8,622,909 B1* | 1/2014 | O'Ruanaidh et al. ......... 600/437 |
| 8,846,040 B2 | 9/2014 | Imran |
| 8,911,425 B2 | 12/2014 | Dijksman et al. |
| 2002/0167313 A1 | 11/2002 | Taimisto |
| 2002/0173718 A1* | 11/2002 | Frisch et al. ................. 600/424 |
| 2004/0068204 A1* | 4/2004 | Imran et al. .................. 600/593 |
| 2004/0143182 A1 | 7/2004 | Kucera et al. |
| 2004/0181127 A1 | 9/2004 | Matsumoto et al. |
| 2004/0210131 A1* | 10/2004 | Fukuda et al. ............... 600/424 |
| 2005/0064815 A1 | 3/2005 | Kanazawa |
| 2005/0104776 A1* | 5/2005 | Anderson .................... 342/450 |
| 2007/0282252 A1 | 12/2007 | Stukanov |
| 2008/0009711 A1 | 1/2008 | Govari et al. |
| 2008/0063703 A1 | 3/2008 | Gross et al. |
| 2008/0269664 A1 | 10/2008 | Trovato et al. |
| 2008/0312501 A1 | 12/2008 | Hasegawa et al. |
| 2009/0192348 A1 | 7/2009 | Nishino |
| 2010/0049012 A1 | 2/2010 | Dijksman et al. |
| 2010/0222670 A1 | 9/2010 | Demierre et al. |
| 2010/0331827 A1 | 12/2010 | Shimizu |
| 2011/0071385 A1* | 3/2011 | Bouchoucha ................ 600/424 |
| 2011/0125007 A1 | 5/2011 | Steinberg et al. |
| 2011/0148714 A1 | 6/2011 | Schantz et al. |
| 2011/0319749 A1 | 12/2011 | Wang et al. |
| 2012/0116358 A1 | 5/2012 | Dijksman et al. |
| 2013/0204233 A1 | 8/2013 | Zou et al. |
| 2015/0011874 A1 | 1/2015 | Amoako-Tuffour et al. |

FOREIGN PATENT DOCUMENTS

| | | |
|---|---|---|
| CN | 101352343 | 1/2009 |
| CN | 100588378 | 2/2010 |
| EP | 1 502 545 | 7/2004 |
| IL | 175930 B | 12/2012 |
| WO | WO 2007/074445 | 7/2007 |
| WO | WO 2007/110270 | 10/2007 |
| WO | WO 2008/120156 | 10/2008 |
| WO | WO 2009/063375 | 5/2009 |
| WO | WO 2010/004555 | 1/2010 |

OTHER PUBLICATIONS

Hiroz, et al., Colonic Movements in Healthy Subjects as Monitored by a Magnet Tracking System, Neurogastroenterol Motil (2009) 21, in 10 pages.

Alonso, et al., Enabling Robotic Functions in an Endoscopic Capsule, Universitat de Barcelona, May 27, 2010 in 19 pages.

Yadav, Nikku, "*Intelligent Pills*," Pharmainfo.net, Aug. 12, 2009, in 12 pages. http://www.pharmainfo.net/nikkuyadav/publications/intelligentpills.

"*IntelliCap®—Electronic Capsule for Personalized Oral Controlled Release*," MediMetrics, Apr. 18, 2012, in 8 pages.

Hosseini, Saman, "*Design, Fabrication and Control of a Magnetic Capsule Robot for the Human Esophagus*," A thesis presented to the University of Waterloo, Ontario, Canada, 2009, in 115 pages.

Lambert, et al., "*Autonomous Telemetric Capsule to Explore the Small Bowel*," Medical and Biological Engineering and Computing, vol. 29, Issue 2, pp. 191-196, Mar. 1, 1991, in 6 pages.

Caffrey, et al., "*Swallowable-Capsule Technology*," Tyndall National Research Institute, IEEE CS, Jan.-Mar. 2008, in 7 pages.

Trafton, Anne, "*Successful Human Tests for First Wirelessly Controlled Drug-Delivery Chip*," MIT News, Feb. 16, 2012, in 3 pages.

Tebrean, et al., "*Novel Drug Delivery Systems—Method Review*," Acta Electrotehnica vol. 52, No. 1, Jan. 21, 2011, in 7 pages.

Fassov, et al, "*A randomized, controlled study of small intestinal motility in patients treated with scral nerve stimulation for irritable bowel syndrome*," BioMed Central, Dec. 6, 2013, in 8 pages. http://www.biomedcentral.com/1471-230X/14/111.

Haase, et al., "*Pilot study trialling a new ambulatory method for the clinical assessment of regional gastrointestinal transit using multiple electromagnetic capsules*," Neurogastroenterology & Mobility, Oct. 27, 2014, in 9 pages.

* cited by examiner

Example Circuit Model of Pill

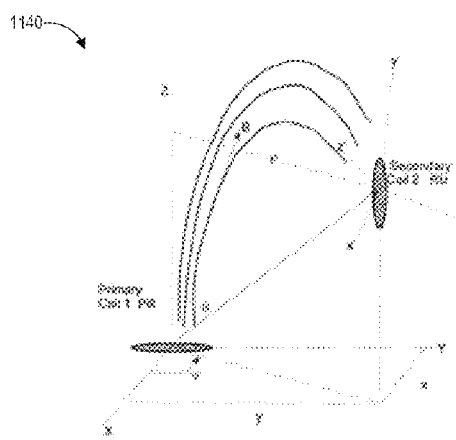 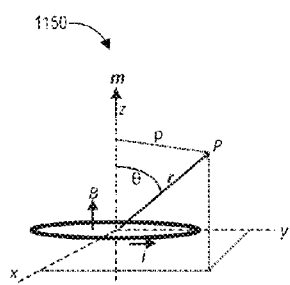
FIG. 11B   FIG. 11C

SYSTEM AND METHODS FOR LOCATING RELATIVE POSITIONS OF MULTIPLE PATIENT ANTENNAS

RELATED APPLICATIONS

This application claims priority under 35 U.S.C §119(e) as a nonprovisional of U.S. Provisional Application No. 61/784,340, filed Mar. 14, 2013, titled SYSTEM FOR LOCATING RADIOFREQUENCY TRANSCEIVER IN THE HUMAN BODY, and U.S. Provisional Application No. 61/683,851, filed Aug. 16, 2012, titled MOTILITY PILL GASTROINTESTINAL MONITORING SYSTEM. The disclosures of each of the foregoing applications are hereby incorporated by reference in their entirety.

BACKGROUND

Movement of food through the human digestive tract can be obstructed or slowed for a variety of reasons. Frequently, there may be little or no pain, yet the condition may result in death if the condition is not identified and treated quickly. Reasons for gastrointestinal (GI) dismotility are numerous, including bowel strangulation, neuropathy, diverticulitus, paraplegia, diabetic gastroparesis, chemotherapy, mental conditions, and drug interaction. People of some or all ages can be affected, ranging from newborn babies to the elderly.

SUMMARY

For purposes of summarizing the disclosure, certain aspects, advantages and novel features have been described herein. It is to be understood that not necessarily all such advantages can be achieved in accordance with any particular embodiment disclosed herein. Thus, the embodiments disclosed herein can be embodied or carried out in a manner that achieves or optimizes one advantage or group of advantages as taught or suggested herein without necessarily achieving others.

In certain embodiments, a method of locating a plurality of antennas positioned about a body of a patient can include generating a transmit signal for transmission from any of a plurality of antennas, the plurality of antennas positioned about a body of a patient. The method can also include providing the transmit signal to at least some of the plurality of antennas to cause at least some of the antennas to transmit the transmit signal. In some embodiments, the method can include receiving a set of receive signals from the antennas, the receive signals responsive to the transmit signal. Furthermore, the method can also include determining relative phase shifts among the receive signals. In some embodiments, the method can include estimating relative locations of the antennas based at least in part on the relative phase shifts. Moreover, the method can include using the estimated relative locations of the antennas to calculate a position of a pill transmitter swallowed by the patient. The method can include outputting the position of the pill transmitter for presentation to a clinician on a display. In some embodiments, at least said estimating relative locations of the antennas is performed by processing electronics.

Additionally, in certain embodiments, a system for locating a plurality of antennas positioned about a body of a patient can include an array of antennas configured to be positioned about a body of a patient. The system can include processing electronics to generate a transmit signal for transmission from the array of antennas. The processing electronics can further provide the transmit signal to a first antenna of the array of antennas to cause the first antenna to transmit the transmit signal. The processing electronic can also receive a set of receive signals from second antennas of the array of antennas, the receive signals responsive to the transmit signal. In some embodiments, the processing electronics can estimate relative locations of the antennas based at least in part on an analysis of the receive signals. The processing electronics can use the estimated relative locations of the antennas to calculate a position of a pill transmitter swallowed by the patient.

In certain embodiments, an apparatus for locating a plurality of antennas positioned about a body of a patient can include processing electronics that can dynamically calculate positions of antennas located about a body of a patient to account for movement of the body of the patient. The processing electronics can provide a first transmit signal to the antennas at a first time. The processing electronics can also receive first receive signals from the antennas, the first receive signals responsive to the first transmit signal. Furthermore, the processing electronics can estimate first relative locations of the antennas based on an analysis of the first receive signals. The processing electronics can also provide a second transmit signal to the antennas at a second time subsequent to the first time. Moreover the processing electronics can receive second receive signals from the antennas. In some embodiments, the processing electronics can estimate second relative locations of the antennas based on an analysis of the second receive signals, the second relative locations different from the first relative locations. The apparatus can also include a memory device that can store data representing the first and second relative locations of the antennas.

BRIEF DESCRIPTION OF THE DRAWINGS

Throughout the drawings, reference numbers are re-used to indicate correspondence between referenced elements. The drawings are provided to illustrate embodiments of the features described herein and not to limit the scope thereof.

FIGS. 11B and C illustrate model diagrams for antenna interactions in accordance with an embodiment of the disclosure.

DETAILED DESCRIPTION

Figure 1A:
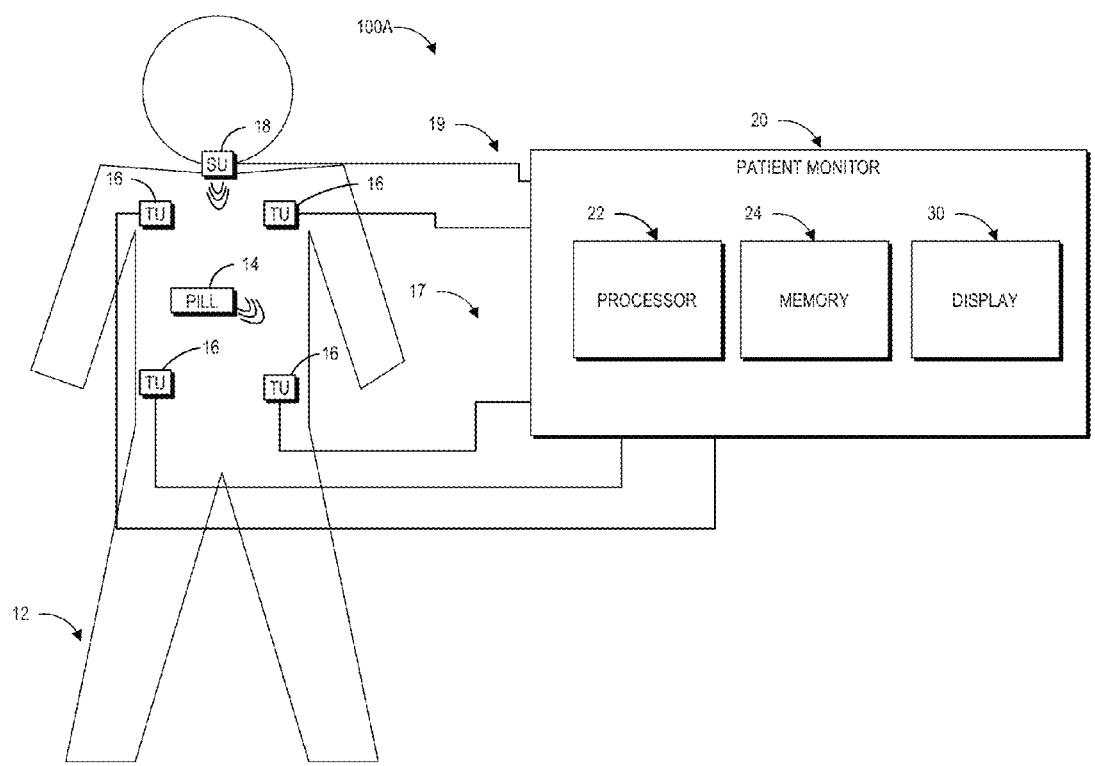
FIGS. 1A-B are block diagrams illustrating transponder monitoring systems in accordance with embodiments of the disclosure.

Various embodiments will be described hereinafter with reference to the accompanying drawings. These embodiments are illustrated and described by example only, and are not intended to be limiting.

I. Problems with Current GI Tract Monitoring Techniques

For the past decade, the gastrointestinal ("GI") tract has become an area of intense scientific and public interest due to exciting discoveries of its importance in many aspects of human health and disease. However, understanding the pathophysiology of many gastrointestinal disorders is hampered by an inadequate ability to investigate primary GI functions with a technological means providing low patient stress, rapid and effective diagnostic data, and ease of use enabling universal adoption.

Science's limited knowledge of various GI problems is especially evident in the expanding obese population who are at high risk of developing diabetes mellitus. Diabetic patients frequently suffer from gastrointestinal dysmotility such as gastroparesis, a functional delay in the emptying of the stomach in the absence of mechanical obstruction. Symptoms usually include early satiety, nausea, vomiting, bloating, and may be associated with erratic blood sugar control due to variable stomach emptying. These symptoms afflict as many as 12% of the diabetic population and are only assumed to be resultant from gastroparesis. At this time, the diagnostic tools to prove certainty are unavailable.

Outside the diabetic group, many other patient populations could immediately benefit from a safer, more readily available, and more precise technology to evaluate GI function as it relates to feeding intolerance. These populations are wide ranging and include infants, post-surgical patients, mechanical obstruction patients, and those in Intensive Care Units. This group alone engenders a substantial financial impact due to both increased length of hospital stay and morbidity and mortality due to nutritional inadequacies. Feeding intolerance and presumed GI dysmotility, including chronic constipation, is frequently reported in children with (and infants at risk for) Autism Spectrum Disorder. Patients can spinal cord injuries (SCI) would greatly benefit in quality of life with a real-time motility monitoring system. Patients with endocrine disorders such as hypo/hyperthyroidism, pituitary and parathyroid disease, and Addison's disease; as well as large percentages of the population with functional dyspepsia, refractory irritable bowel syndrome, post-infectious and idiopathic gastroparesis, narcotic bowel syndrome and Oglevie's syndrome would also benefit from improved GI tract diagnosis technology.

The inadequacy of our current technical ability to evaluate GI tract pathophysiology is hindering diagnosis and treatment. If we can diagnose and understand the problems more intricately and with greater fidelity, we can be able to develop new nutritional, pharmacologic, electromechanical, and surgical solutions to treat them. In doing so, we can significantly improve the quality of life of those afflicted.

Initial diagnosis of problematic gastric emptying can be tested to rule out obstruction. Typically this is performed either invasively via upper endoscopy or externally using barium X-ray techniques entailing radiation exposure. Today, nuclear scintigraphy is the gold standard for estimating gastric emptying. This utilizes ingestion of a radioisotope (Tc-99m sulfur colloid) labeled egg salad sandwich followed by scintiscanning every 15 minutes for 4 hours. This subjects the patient to radiation exposure equal to ⅓ of what is experienced annually from natural sources (USA) and involves very expensive specialized equipment and expertise.

Alternate diagnostic procedures for assessing gastric emptying use radio-opaque markers tracked through serial X-ray imaging. Although simple and relatively inexpensive, this method measures the emptying of large non-digestible markers instead of physiologically relevant solids which only provides a partial indicator of the situation. A breath test is also available to estimate gastric emptying after a radioisotope-labeled meal is ingested. The stable isotope, usually $^{13}CO_2$, is incorporated into the carbon dioxide exhaled which can be recovered and sent to a reference laboratory for determination.

There are existing radiofrequency (RF) location techniques that use the returned power from a wireless transmitting tag to estimate location by radio direction finding. The technique is not accurate, doing only a very rough 2-dimensional (2D) tag location. Lastly, there is limited experience in bowel motility evaluation with a device called the SmartPill™ by Given Imaging™. This device utilizes pH, temperature and pressure data to determine a very rough position in the bowel. This device is too large to be treated in the same manner as food particles by the stomach, thus limiting its usefulness, especially in pediatric populations. Another pill device available from Given Imaging™, called the PillCam™, performs a capsule endoscopy to obtain GI tract video. The PillCam™ is also a relatively large pill and does not provide any location-finding mechanism.

II. Proposed Solution Overview

Prior methods for monitoring GI tract health typically fail to provide a means to continuously monitor GI peristalsis and/or motility health and do not support this monitoring in a home or care facility environment. It would be beneficial to provide a highly effective, simple to implement, and inexpensive monitoring system to measure GI motility and general GI tract function. Certain embodiments of the systems described herein can provide some or all such benefits, overcome shortfalls of existing monitoring solutions, can be applicable to a variety of healthcare applications, and can be flexible and extendable to the treatment, research, and monitoring of many other GI diseases and conditions.

Embodiments of systems and methods described herein are designed to monitor the movement of one or more swallowed pill transducers through the human GI tract or digestive system, including the mouth, esophagus, stomach, large and small intestines, colon, and rectum, or any subpart thereof. These systems and methods can include hardware and/or software that can accurately track and record the movement of the pill or pills as they move through the GI tract to ultimate elimination. An external sensor system, which may include antennas, enables position tracking and/or flow rate of the pill(s) through the GI tract. The antennas can provide signals indicative of pill position to a processor, which can perform signal processing to determine pill location, flow rate, motility, or any of a variety of other measurements related to the pill(s). The processor can provide such measurements and information to a display (local to the processor or over a network, such as to a cellphone or personal digital assistant (PDA)) for presentation to a clinician, such as a physician, nurse, or other care personnel.

For example, in one embodiment, the systems and methods described herein use near field communications to locate a radiating transponder, such as a pill swallowed by a patient. The system can be triggered to turn on and transmit an amplitude shift keyed waveform (or other type of waveform) to a set of antennas attached to, coupled with, or near the patient at roughly known locations. The magnetic field emitted by the transponder can be measured by the receiving antennas, for example, using principles of mutual inductance. The receiving antennas may be tuned specifically to the frequency of the emitting transponder for high sensitivity and high Q. The differential phase and/or time shifts between the antennas can contain sufficient information to find the location of the transponder and optionally its orientation relative to body coordinates. The system can display the location and/or orientation of the transponder and may optionally provide other information about the movement, flow, or other characteristics of pill to assist clinicians with diagnosis.

In addition, in some embodiments, the pill may also include one or more additional sensors that output data, which the pill can transmit to the receiving antennas for processing by the processor. Examples of such sensors include pressure sensors, pH sensors, temperature sensors, camera(s), salinity sensors, and the like. In other embodiment, however, at least some of such sensors are omitted to reduce the size of the pill, thereby enabling the pill to be small and compact. With its small and compact shape, the pill can act like food particles and therefore more accurately represent digestive activity of a patient than current larger pill transponders. Further, different size pill transponders that act like different sizes of food particles can be swallowed by a patient and analyzed by the processor to provide a more comprehensive view of digestive activity for presentation to a clinician.

Thus, the systems and methods described herein can provide clinicians with the ability to identify obstructions, regurgitations, reflux, or other GI conditions that are dangerous to a patient's health and which are currently difficult if not impossible to monitor in a simple, low cost, and non-invasive manner. Thus, the systems and methods described herein can facilitate diagnosing and/or treating numerous diseases and conditions, including, but not limited to, Crohn's disease, bowel strangulation, neuropathy, diverticulitis, paraplegia-related conditions, diabetic gastroparesis, functional dyspepsia, irritable bowel syndrome, epigastric pain syndrome, and post infectious and idiopathic gastroparesis. Further, the systems and methods described herein can facilitate treating patients with endocrine disorders such as hypo-/hyperthyroidism, pituitary and parathyroid disease, and Addison's disease.

III. Example Transponder Monitoring System Overview

Prior to describing transponder location measurements in detail, an overview of example transponder monitoring system is provided below with respect to FIGS. 1 and 2. The transponder monitoring system can include a transponder (e.g. pill) and a plurality of antennas. The transponder monitoring system can track location of the pill with respect to the plurality of antennas. In some embodiments, the transponder monitoring system can also automatically track the positions of the plurality of the antennas For example, FIG. 1 shows an embodiment of a physiological monitoring system 100. In the physiological monitoring system 100, a medical patient 12 can ingest a pill 14, which can be tracked by a patient monitor 20. The pill 14 can include one or more antennas to transmit signals as it passes through the GI tract of the patient 12. In an embodiment, the pill 14 transmits a signal in response to a trigger signal from a stimulus antenna 18. The stimulus antenna 18 can be positioned on the patient or with the patient monitor or in a room. The patient monitor 20 can control the operation of the stimulus antenna via a link 19. The plurality of transceiver units (TU) 16 can also include one or more antennas to receive the transmitted signals from the pill 14. In one embodiment, the system includes 5 TUs. In other embodiments, the system can include 10, 20, 50, or 100 TUs. Increasing the number of TUs can improve accuracy of measurements, but might require more processing.

The patient monitor 20 can collect the received signals from the plurality of receiving units 16 via a link 17 for processing by one or more processors 22. Links 17 and 19 can include wired or wireless (Bluetooth, NFC, WiFi or like) communication. The processor 22 can implement one or more modules for calculating the location of the pill 14 in the body of the medical patient 12. The location of the pill 14 can be tracked over time and stored in a memory 24 of the physiological monitor 20.

The processor 22 can communicate the processed signals or measurements to a display 30 if a display is provided. The display 30 can show real time position (in 2 or 3 dimensions) of the pill in the GI tract of the patient 12 (as seen more in detail with respect to FIG. 10). In other embodiments, the position of the pill on the display may be updated periodically (e.g. every 1 second, 30 seconds, 1 minute, 5 minutes, 30 minutes, etc). The update frequency of the display may be a function of the frequency of trigger signals. In an embodiment, the display 30 is incorporated in the physiological monitor 20. In another embodiment, the display 30 is separate from the physiological monitor 20. For example, the physiological monitor 20 can transmit the processed signals over a network to the display 30. The physiological monitoring system 100 is a portable monitoring system in one configuration.

In some embodiments, the plurality of TUs 16 are removably attached at or near the body of the patient 12. In certain other embodiments, a frame (not shown) may structurally support the plurality of TUs 16. Accordingly, the patient 12 can be positioned within the frame structure. The TUs 16 may also be affixed on a bed frame. The strength of the transmitted signals from the pill 14 is inversely proportional with distance. Thus, in some embodiments, the TUs 16 are placed in close proximity to the body of the patient 12 or attached directly to the body or to object in close proximity of the patient 12. For example, the TUs 16 can be attached to bed sheets or mattresses. The TUs 16 can also be attached to the clothing of the patient, such as a vest or an undershirt. The TUs 16 may be attached, for example, with an adhesive. In some embodiments, the TUs can be sewn or staples with the materials.

Figure 1B:
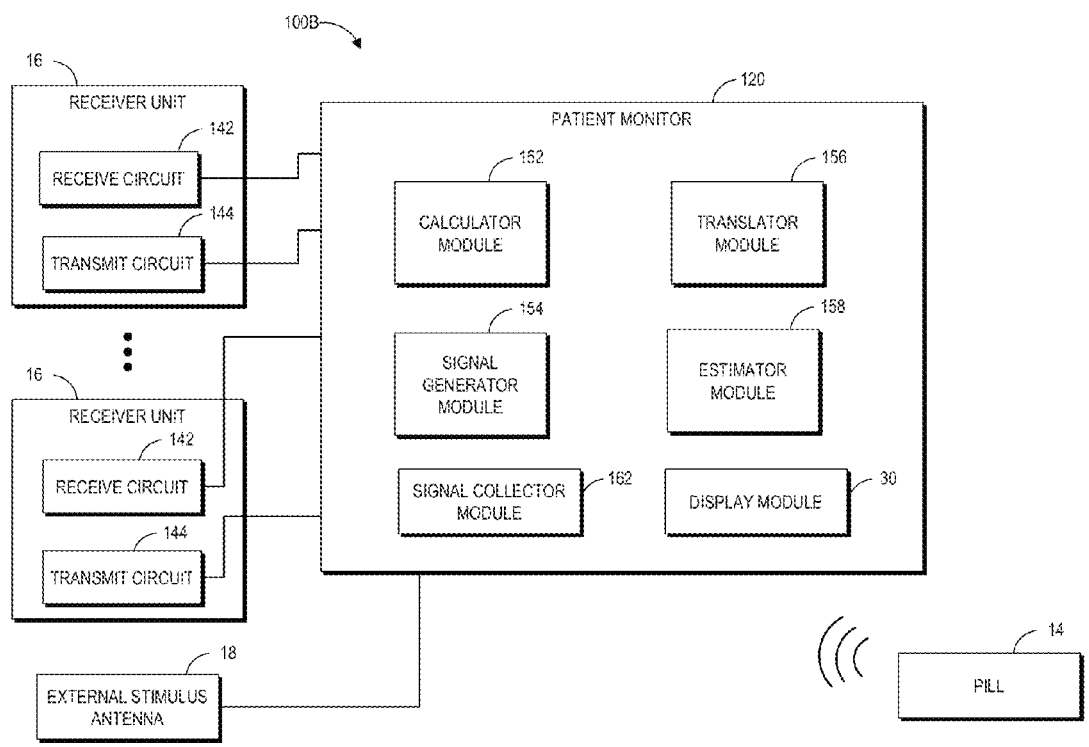

FIG. 1B illustrates a block diagram of an embodiment of the physiological monitoring system 1008. The transceiver units 16 include a receive circuit 142 for receiving signals from the pill 14. In some instances, the transceiver units 16 may further include a transmit circuit 144. The transmit circuit 144 and the receive circuit 142 may include an antenna. In some embodiments, the transmit and receive circuitries can share a common antenna.

In an embodiment, the pill 14 can also include transmit and/or receive circuitry as described more in detail below with respect to FIG. 2A. The pill can transmit a signal waveform in response to receiving a trigger signal from the stimulator antenna 18. The signal generator module 154 of the physiological monitor 20 can instruct the stimulator antenna 18 via the link 19 to transmit the trigger signals. In an embodiment, the signal generator module 154 can generate the trigger signal waveforms. The trigger signals may be generated over a predefined time interval (e.g. every 1 second, 30 seconds, 1 minute, 5 minutes, 30 minutes, etc). The time interval may have a pattern or can be randomized. In some embodiments, users can control the generation of trigger signal via the physiological monitor 20. The trigger signals may also be generated depending on the location of the pill in the patient 12. For example, in a slow moving section of the GI tract, the frequency of triggers signals may be lower than in a fast moving section of the GI tract. In some embodiments, the pill may transmit the signal waveform without continuously requiring external trigger signal. For example, a first trigger signal may activate the pill 14 and thereafter the pill 14 may emit a waveform once every predetermined time interval for a particular duration. The first trigger signal can be received wirelessly or via a switch.

The signal collector module 162 of the physiological monitor 20 can collect the signal waveforms, transmitted by the pill 14, from the transceiver units 16. The phases of the received signals at TUs 16 may vary according to the time it takes the transmitted waveform to travel from the pill to the TU 16. The travel time (or time of flight) is also a function of the distances between the pill and the TUs 16. As such, the phase shifts in the received signals at the first and the second TU may vary depending on the relative locations of the TUs 16. In some embodiments, the calculator module 152 of the physiological monitor 20 can obtain the phase and the amplitude shifts from each of the collected signals. The calculator module 152 can calculate the location of the pill 14 in the patient 12 by applying one or more rules, analysis, and/or filtering on the phase and/or amplitude shifts.

In some embodiments, the location of the pill 14 can be calculated from the phase differences between the received signals at one or more pairs of the TUs 16. For example, a first TU 16 can receive a transmitted signal from the pill 14. A second TU 16 can also receive the same transmitted signal from the pill 14. In certain embodiments, the calculator module 152 can calculate the location of the pill 14 in the patient 12 by applying one or more set of rules on the phase differences between the first and the second TUs. The calculator module 152 can also apply one or more of rules on a combination of measured parameters—phases, amplitudes, and phase differences—to calculate the location of the pill 14. In some embodiments, the measured parameters can be obtained from application of signal processing techniques on the received signals.

The rules can include linear, non-linear, or a combination of linear and non-linear set of operations. In some embodiments, an estimator module 158 may use one or more linear operations to calculate an estimate for the location of the pill 14. The calculator module 152 may then use the estimate in one or more non-linear operations to calculate a more accurate location for the pill 14. In certain embodiments, a calibration process, described more in detail below, can improve the calculation for pill location by calibrating one or more system parameters, such as pill design, TU design, location of the TUs, and the orientation of the TUs. Calibration may be performed with a training data set. In certain embodiments, the physiological monitoring system 100 can adaptively calibrate the system parameters while tracking the pill 14 through the GI tract of the patient. Adaptive calibration can include automatically tracking the location and/or orientation of the TUs 16. As described above, TUs may be attached to a patient. Accordingly, the positions and orientations of the TUs 16 may change with patient movement and the shift in TU positions may affect the quality of pill tracking. Adaptive calibration can be made an instant before the TU locations are used to find the location of the pill.

Automatically monitoring the positions of plurality of TUs 16 can increase the accuracy of pill tracking. As described above, TUs 16 may also include a transmitter circuit 144 for transmission of a signal waveform. The signal generator module 154 can generate a plurality of transmit signals for transmission in a first order from the plurality of TUs 16. In an embodiment, the signals are transmitted one at a time from the plurality of TUs 16. For example, a first TU 16 may transmit a first transmit waveform. The plurality of non-transmitting TUs can receive the first transmitted waveform, which can be collected by the signal collector module 162. Subsequently, a second TU 16 may transmit a second transmit waveform. In some embodiments, the first and the second transmit waveforms are substantially similar. Again, the plurality of non-transmitting TUs 16 can receive the second transmit waveform, which can also be collected by the signal collector 162. The process can continue for each of the plurality of TUs 16. In certain embodiments, a subset of the plurality of TUs 16 may be used to transmit signals. The signal collector module 162 can collect, for each transmitted signal, signals received at plurality of the non-transmitting antennas via links 17. The calculator module 152 can apply one or more rules, analysis, and/or filtering on the collected signals to calculate the location of the plurality of TUs. In some embodiments, the rules can include a modified set of operations from a multilateration analysis.

IV. Example Pill Transponder Embodiments

Figure 2A:
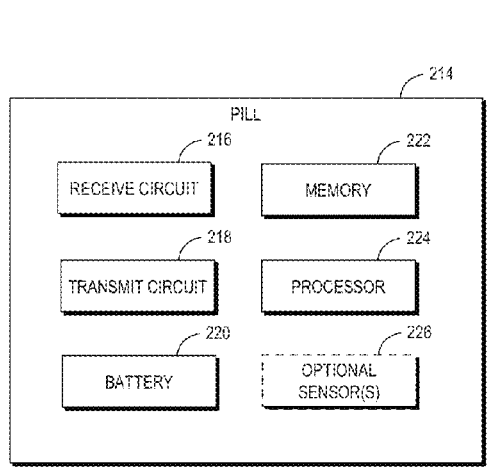
FIG. 2A is a block diagram illustrating a transmitter pill in accordance with an embodiment of the disclosure.

FIG. 2A illustrates an example block diagram of an embodiment of a pill 14 that can be ingested by a patient. The pill 14 can include a transmitter circuit 218 including an antenna for transmitting a signal waveform. While described herein as a transponder, the pill may be a transmitter without receive functionality in some embodiments. In some embodiments, the pill 14 can transmit a signal waveform in response to an external trigger signal. The receive circuit 216 in the pill 14 can also include an antenna to receive the trigger signal from the external stimulator antenna. The receive circuit 216 and the transmit circuit 218 may share an antenna. The antenna may be referred to or be configured as a loop antenna. The antenna may also be referred to or be configured as "magnetic antenna" or an induction coil. The antenna may also include a coil of a type that can wirelessly output or receive wireless communication signals. In some embodiments, the antennas may also wirelessly output or receive power. The pill can also include commercially available or custom RFID tag. In some embodiments, the pill can operate in a passive mode of operation. In the passive mode of operation, the pill may not require a battery or power storage device 220. The external trigger signal can provide sufficient power to the pill for transmitting the signal waveform. The pill may also operate in an active mode or battery-assisted passive mode, requiring an on-board battery or a power storage device 220. In the battery-assisted passive mode, the on-board battery 220 can be smaller than in the active mode.

In the active mode, the pill 14 can be configured to periodically transmit the waveform signal. The pill 14 may transmit the signals based on a predetermined time intervals. For example, after receiving an external stimulus (before or after ingesting the pill), the pill can transmit a signal waveform over a time interval (e.g. every 1 second, 30 seconds, 1 minute, 5 minutes, 30 minutes, etc). The pill may also transmit the signal waveform continuously but that may increase the power duty cycle. In some embodiments, the external signal can be a mechanical switch. The switch may be turned on before ingesting the pill causing it to periodically transmit a signal waveform. The on-board battery may provide sufficient power for the pill to transmit the signals over a span of several days.

In the passive or battery-assisted passive mode, the pill 14 can transmit a signal waveform in response to receiving the trigger signal. The circuitry in the pill can activate in response to the trigger signal and transmit a signal waveform. The pill 14 can then go into a passive state until the next trigger signal is received. In certain embodiments, the physiological monitor 20 can control the generation of trigger signals and transmission from the external stimulus antenna. The trigger signals may be generated over a time interval, for instance, every 1 second, 30 seconds, 1 minute, 5 minutes, 30 minutes, etc.

The waveform characteristics of the transmit signal can be stored in a memory 220 of the pill 14. The waveform characteristics can also be defined by the circuit elements of the transmit circuitry 218. In some embodiments, the transmit waveform can correspond to the characteristics of the trigger signal. The transmit waveform can also be modulated to reduce interference from external signals. Some of the modulation techniques can include Amplitude Shift Keying, Phase Shift Keying, or Frequency Shift Keying. In an embodiment, the duration of the transmit waveform is 1 ms. In other embodiments, the duration of the transmit waveform can be 0.1 ms, 10 ms, 100 ms. The pill may also the transmit the signal continuously.

The frequency characteristics of the transmit waveform can depend on several parameters. For example, at higher frequencies of more than 20 MHz, absorption of the signal waveform by the body tissue and organs may become significant. Furthermore, far field circuit antennas, may require precisely tuned GHz circuitry resulting in complex and expensive system. Near field coupling can allow for simpler electronics and communication via lower frequencies in the range of MHz. In an embodiment, the frequency of the transmit waveform is approximately 13.56 MHz which is part of the industry, scientific, and medical (ISM) radio band. At this frequency, there may be some absorption, but the transmit waveform can pass through 10 cm of body. In another embodiment, the frequency of the transmit waveform is approximately 125 KHz. In yet another embodiment, the frequency of the transmit waveform is 6.8 MHz. At lower frequencies, the absorption from the body may be significantly reduced. In other embodiments, any frequency below 20 MHz may be used to reduce absorption. Frequencies equal to or higher than 20 MHz may also be used in certain embodiments. The frequency may also depend on the power constraints of the emitted waveform. For example, there are limits on power emissions of signals defined by industry standards and regulatory agencies to protect human body. Accordingly, in one embodiment, the power of the transmitted waveform is on the order of microwatts, or milliwatts, or 3 watts or less, or some other value.

Figure 2B:
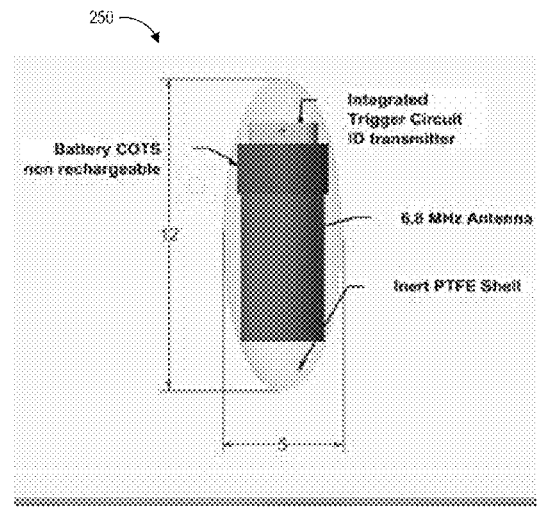
FIG. 2B illustrates a cross section view of a pill transmitter in accordance with an embodiment of the disclosure.

FIG. 2B illustrates a cross-section 250 of an embodiment of a pill transmitter 14. The electronics in the pill can be encapsulated with a material that is suitable for ingestion, for example, polytetrafluoroethylene (PTFE). The size of the pill 14 can vary depending on the size of the circuitry, for example, the size of the battery 220. In an embodiment, the size of the pill 14 is 5 mm×12 mm. For a pill with a smaller battery, the size can be reduced to 4 mm×6 mm capsule. In an embodiment, the antenna includes a ferrite core and has a micro rod design.

One benefit of the shape and size of the pill in certain embodiments is that the pill can be small enough that it acts like food. Thus, the pill can move with food and therefore mimic the motility or GI problems that food is having in the patient's body. The size of the pill is small in certain embodiments because the pill may not have a bulky camera as in other existing pill designs. Existing pills from other manufacturers can actually be so large that they become obstructions themselves. In contrast, in certain embodiments, the pill described herein can be about 6 mm in size or less. Alternatively, the pill may be about 1.2 cm in size or less, or a slightly greater size. The smaller size pill can move with smaller sized bits of food, while the larger sized pill can move with larger bits of food. Different sized pills can therefore be used to diagnose or analyze different illnesses. In fact, different sized pills (including more than 2 different sizes) can be swallowed by the patient and tracked at the same time to track both small food movements and larger food movements. Any number of pills may be swallowed and tracked at one time, for example, up to 5 pills, or up to 10 pills, or up to 24 pills, or up to 48 pills. In one embodiment, detecting solely motility can be accomplished using a single pill, but also detecting obstructions can be accomplished using multiple pills.

Figure 2C:
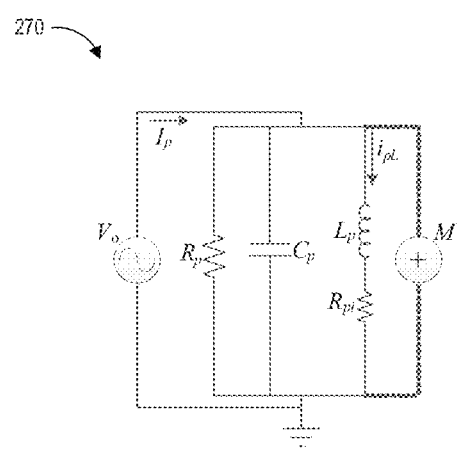
FIG. 2C illustrates a model circuit diagram for the pill transmitter in accordance with an embodiment of the disclosure.

FIG. 2C illustrates a model circuit diagram 270 of an embodiment of a pill 14. The inductor $L_p$ in the conception circuit diagram can be 1 μH and the capacitor $C_p$ can approximately be 150 pF such that $1/\sqrt{L_p C_p} = 2\pi \times 13.0$ MHz. The $R_{pi}$ in series with the inductor can represent the internal wire Ohmic resistance, presumably only a few Ohms. In some embodiments, the model can include a capacitor in series with the RLC circuit. Resistor $R_p$ can represent the eddy current and hysteresis losses in the inductor core. In an embodiment, $R_p$ is in parallel because that better models the measured frequency dependence when driven with a sweep frequency. The $R_p$ value can be greater than 1 kΩ. In the model, the circuit is driven with an oscillator voltage source $V_o$ at some frequency ω. That forces a prescribed voltage across the parallel RLC.

However if an external magnetic field penetrates the area of the entire circuit, or of just the inductor $L_p$, it can induce an additional emf across $L_p$-$R_{pi}$ and so across $R_p$ and $C_p$. Such a magnetic field is provided by mutual inductance M from the currents in the nearby TU antenna circuits as illustrated in FIG. 2C by the dashed source on the right, marked M and "+" to indicate its emf is added to Vo. $I_p$ is the total current drawn from the voltage source by the pill circuit. $I_{pL}$ is the current through the pill inductor $L_p$.

In one embodiment, the pill can be modeled as a radiating magnetic dipole. In another embodiment of the pill, the pill can radiate sequentially through three orthogonal dipole directions, similar to a phased magnetic array (not shown), which gives an almost uniform field for all TUs to measure. Both embodiments can be used to find the location of the pill using the analysis described herein.

V. Transceiver Units

Figure 3:
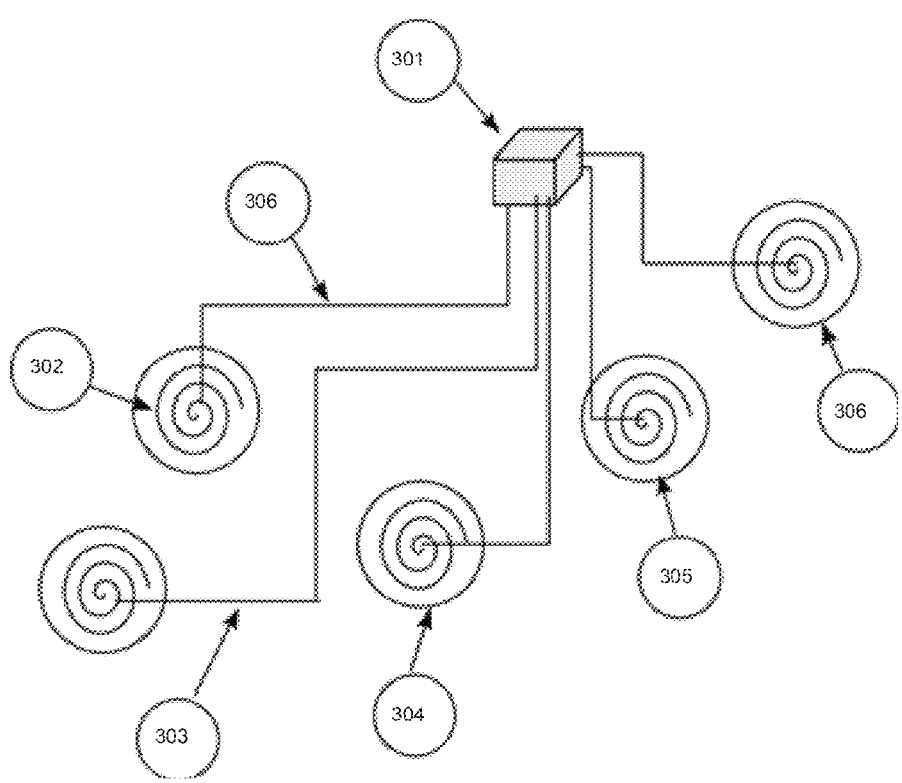
FIG. 3 illustrates a plurality of transceiver units in connection with a patient monitor in accordance with an embodiment of the disclosure.

FIG. 3 illustrates an embodiment of a TU system 300 including a plurality of TUs connected to a communication box 301 via one or more links 310. The links can include wired or wireless type connections. For the wired connections, the links 310 can be arranged a single cable. The cable may be also be shielded. As described above, the TUs 302-306 can include one or more antennas for receiving or transmitting signals. In an embodiment, the communication box 301 can include a patient monitor 20. In another embodiment, the communication box 301 can include a mobile device that collect the received signals from the TUs and transfer the signals to the patient monitor 20. The transfer of the signals from the communication box 310 to the patient monitor 20 can be via a (wired or wireless) network. Accordingly, in one embodiment, the patient can be mobile without carrying the patient monitor.

The antenna may be referred to or be configured as a loop antenna. The antenna may also be referred to or be configured as "magnetic antenna" or an induction coil. The antenna may also include a coil of a type that can wirelessly output or receive wireless communication signals. In some embodiments, the antennas may also wirelessly output or receive power.

VI. Example Pill Location Process

Figure 4:
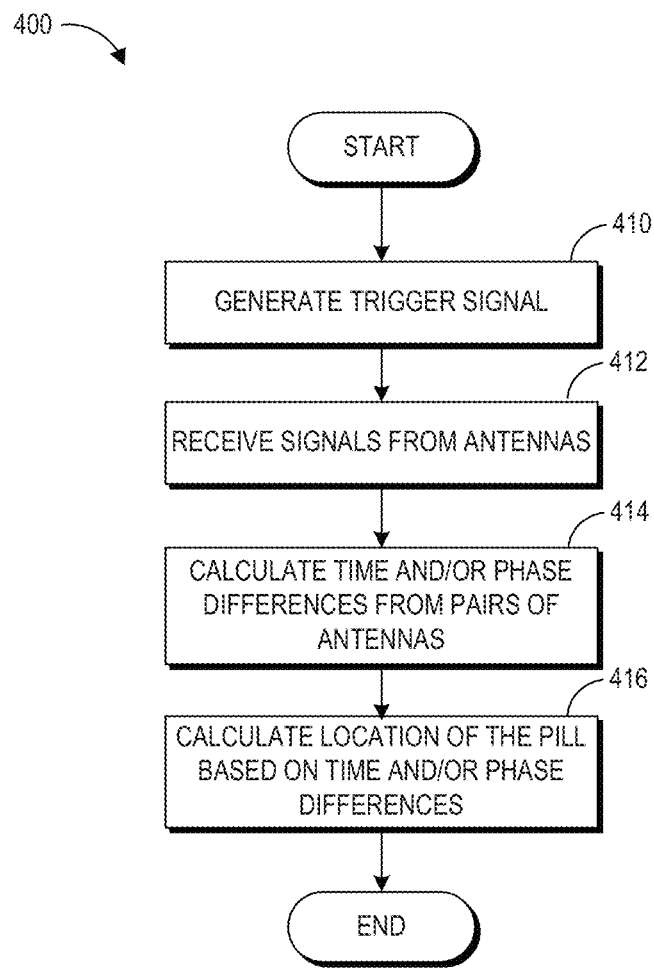
FIG. 4 illustrates an embodiment of a process for calculating the location of a pill transmitter.

FIG. 4 illustrates an embodiment of a process 400 for calculating the location of a pill in the patient 12. This process can be implemented by the system 100 described herein. In particular, each of these processes can be implemented by one or modules in the patient monitor 20 described above. Advantageously, in certain embodiments, these processes can enable monitoring of a pill as it moves through the GI tract of a patient. In some embodiments, the location of the TUs and the coupling coefficients between the antennas are calculated prior to calculating the location of the pill.

Referring specifically to FIG. 4, at block 410, the signal generator module 154 can generate a trigger signal that may be transmitted from an external stimulus antenna 18. The pill 14 can receive the trigger signal and in response transmit a signal waveform. The plurality of TUs 16 can receive the signal waveform transmitted from the pill 14. In some embodiments, the pill 14 can generate the transmit signal without requiring a trigger signal. At block 412, the signal collector module 162 can collect the received signal waveforms from the plurality of TUs 16. The calculator module 152 can analyze the collected waveforms to calculate a first set of measurements at block 414. In an embodiment, the measurement module of the patient monitor 20 can calculate relative phase (or phase shifts) and amplitude measurements for each of the collected signals. In certain embodiments, the measurement module can also measure the phase differences between one or more pairs of collected signals. Then, at block 416, the location calculator module can calculate the location of the pill by applying a first set of rules, analysis, or filtering on the measurements.

The first set of rules can include linear, non-linear, or a combination of linear and non-linear set of operations. In an embodiment, the first set of rules can be applied to an electromagnetic coupling model of the system described more in detail below. In certain embodiments, an estimator module 158 can calculate a first estimate of the pill location. The location calculator module 152 can use the first estimate as a starting set of values to solve for the location of the pill. For example, in certain embodiments, a linear set of operations (e.g. multivariate linear regression) can be used to calculate the location estimate and then the location calculator module can use non-linear operations (e.g. Levenberg-Marquart analysis) to refine the estimated value. As the pill moves through the body, location state vector models may be used to further improve the accuracy of tracking. For example, a Markov chain, Kalman filter, or a combination of Markov chain and Kalman filters can be used to improve tracking. Other tracking filters may also be used. A pill trajectory can be calculated by taking derivative of the pill locations. The trajectory may be shown on the display 30.

The location calculator module 152 can use one or more models to calculate the location of the pill. For example, the calculator module 152 can use electromagnetic coupling model which will be described more in detail below. The location calculator module can also use multilateration analysis on the collected signals for calculating pill locations. The multilateration analysis can be used independently or in conjunction with the electromagnetic coupling model. The location calculator module 152 can take into account secondary coupling effects described below to refine the measurements. In some embodiments, the pill can be accurately located within a 1 cm error margin in three dimensions.

In some embodiments, the location calculator module 152 can calibrate the system by measuring initial system parameters for use in one or more model calculations. The system parameters can include pill geometry, location of the TUs, orientation of the TUs, and other related inherent properties of the system. The location calculator module can apply the system parameters in calculating the location of the pill. The initial calibration (training set) process is described in more detail with reference to FIGS. 9A and 9B. Further, dynamic calibration can modify the initial system parameters by automatically measuring the location of TUs over time as described below.

Figure 5:
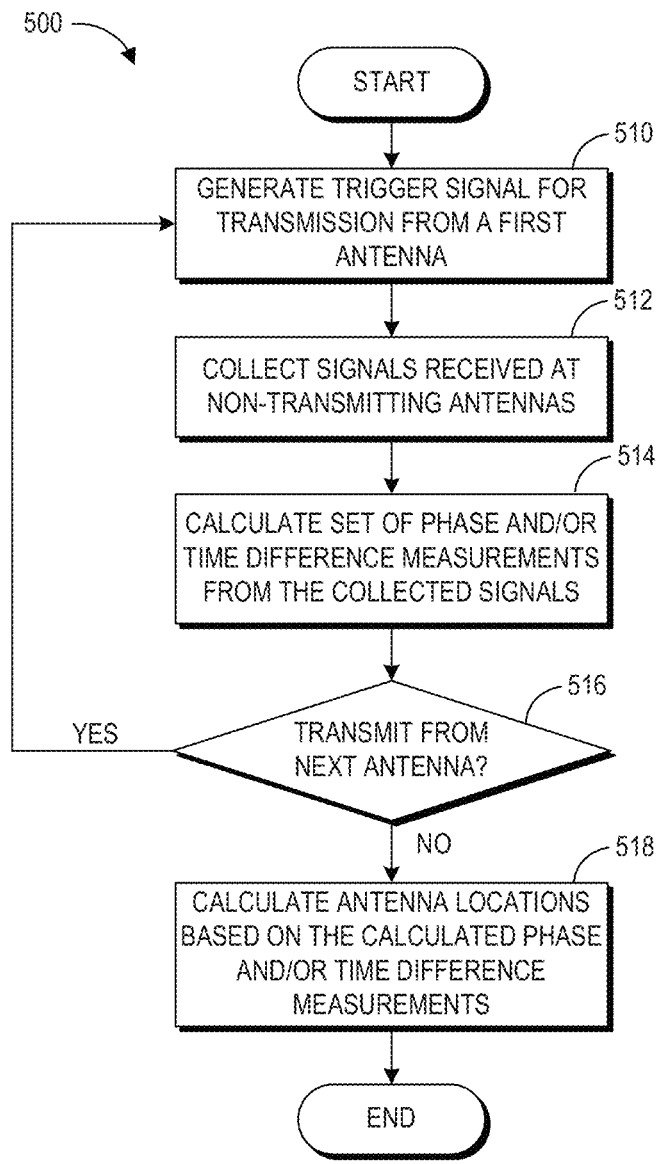
FIG. 5 illustrates an embodiment of a process for dynamically calculating positions of a plurality of antennas.

VII. Example Dynamic Transceiver Antennas (TUs) Position Calculation Process As described above, the plurality of TUs 16 can be affixed, coupled to or placed in proximity with the patient 12. The location and the orientation of TUs may change as the patient moves during the pill tracking process which may run on over several hours or days. Accurately tracking the location of TUs can improve the pill tracking because the pill is tracked as a function of TU coordinates. A translator module 156 can convert the pill location from the TU coordinates to body coordinates for display on a screen. FIG. 5 illustrates an embodiment of a process 500 for calculating TU locations. This process can be implemented by the system 100 described herein. In particular, each of these processes can be implemented by one or modules in the patient monitor 20 described above.

Referring specifically to FIG. 5, at block 510, the signal generator module can generate a transmit signal for transmission from a first TU in the plurality of TUs 16. The non-transmitting TUs in the plurality of TUs 16 can receive the transmitted signal from the first TU. The signal collector module can collect the received signals from the non-transmitting TUs at block 512. The calculator module can process the collected signals and calculate a first set of measurements. The first set of measurements can include one or more of the following: time difference measurements, relative phase shifts measurements, phase differences or amplitude shifts. In some embodiments, the collected signals might be stored for later processing. Thereafter, the process can be repeated for other TUs that have not yet been used for transmitting signals. Once the system has cycled through all or a subset of the plurality of TUs, the calculator module can calculate the location of TUs from all the collected signals and measurements at block 518. In some instances, transmission from one or more may TUs may be repeated. In yet more embodiments, a subset of TUs from the plurality of TU's are used. The location calculator module can apply rules, analysis, or filtering on the set of collected data to calculate the locations. The rules can include a set of linear, non-linear, or a combination of linear and non-linear operators.

In some embodiments, the positions of the TUs can be automatically calculated by a multi-multilateration (MML) process. The MML process builds on the basic idea of multilateration. In the MML process, the phase differences found by sequencing through the TUs can be related to the time difference of arrival after correction for all secondary phase interactions are accounted for. In another embodiment, the multivariate linear regression is used to find the locations without regard to correcting phases from secondary interactions, but by forming a training set that has the secondary interactions included in the training data set. Both embodiments are further discussed in the following paragraphs.

VIII. Multi-Multilateration

Multilateration analysis can be used to calculate a location of a transmitting antenna based on signals received at the plurality of receivers. Multilateration analysis relies on the principal of time difference of arrival (TDOA) of a signal from the emitter at four or more transceiver sites. A multi-multilateration technique can be used to locate plurality of transmitting antennas in relative transmitter coordinates.

Figure 6A:
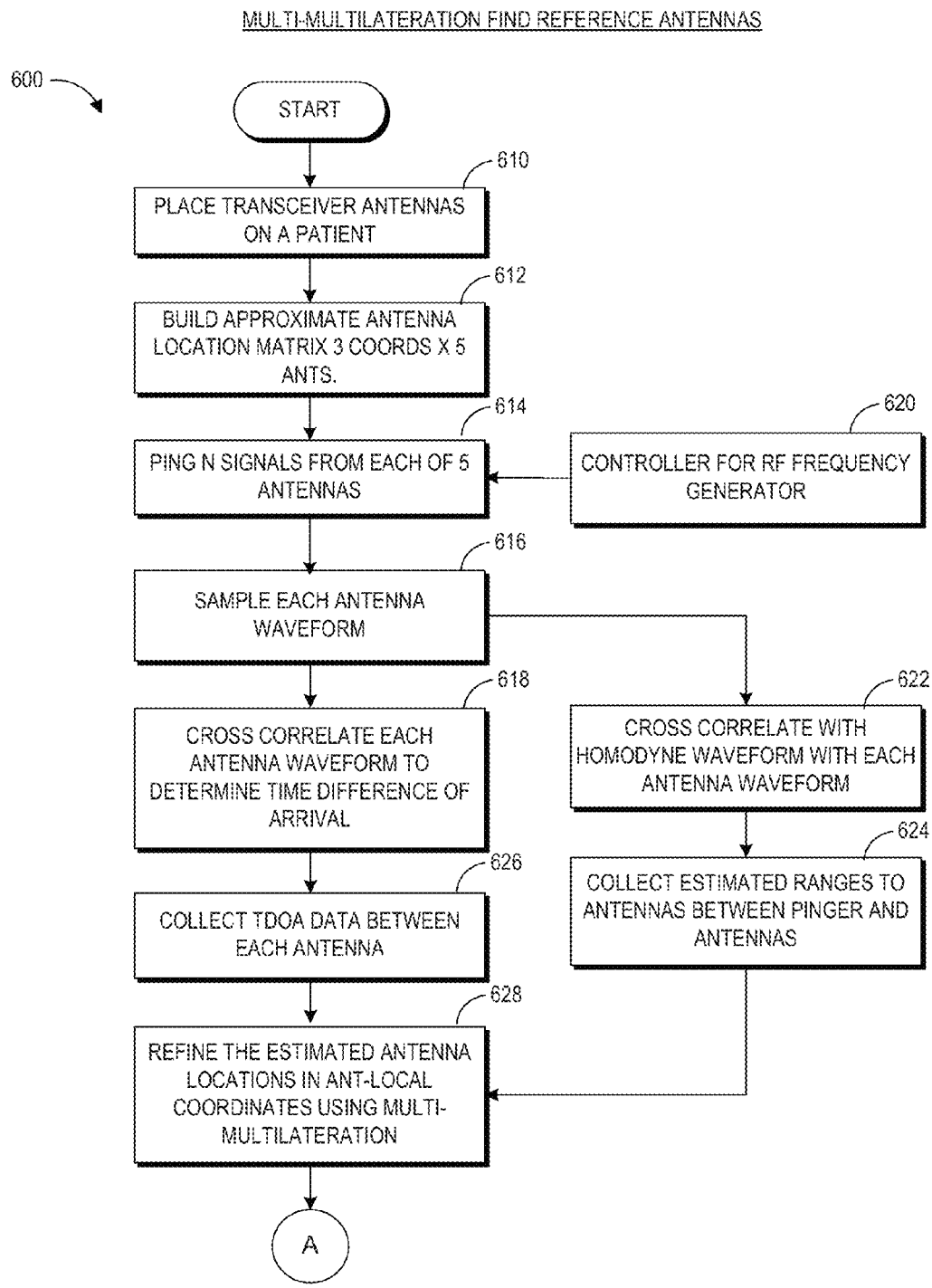
FIGS. 6A and B illustrate an embodiment of a process for using multi-multilateration analysis to dynamically calculate the positions of a plurality of antennas.
Figure 6B:
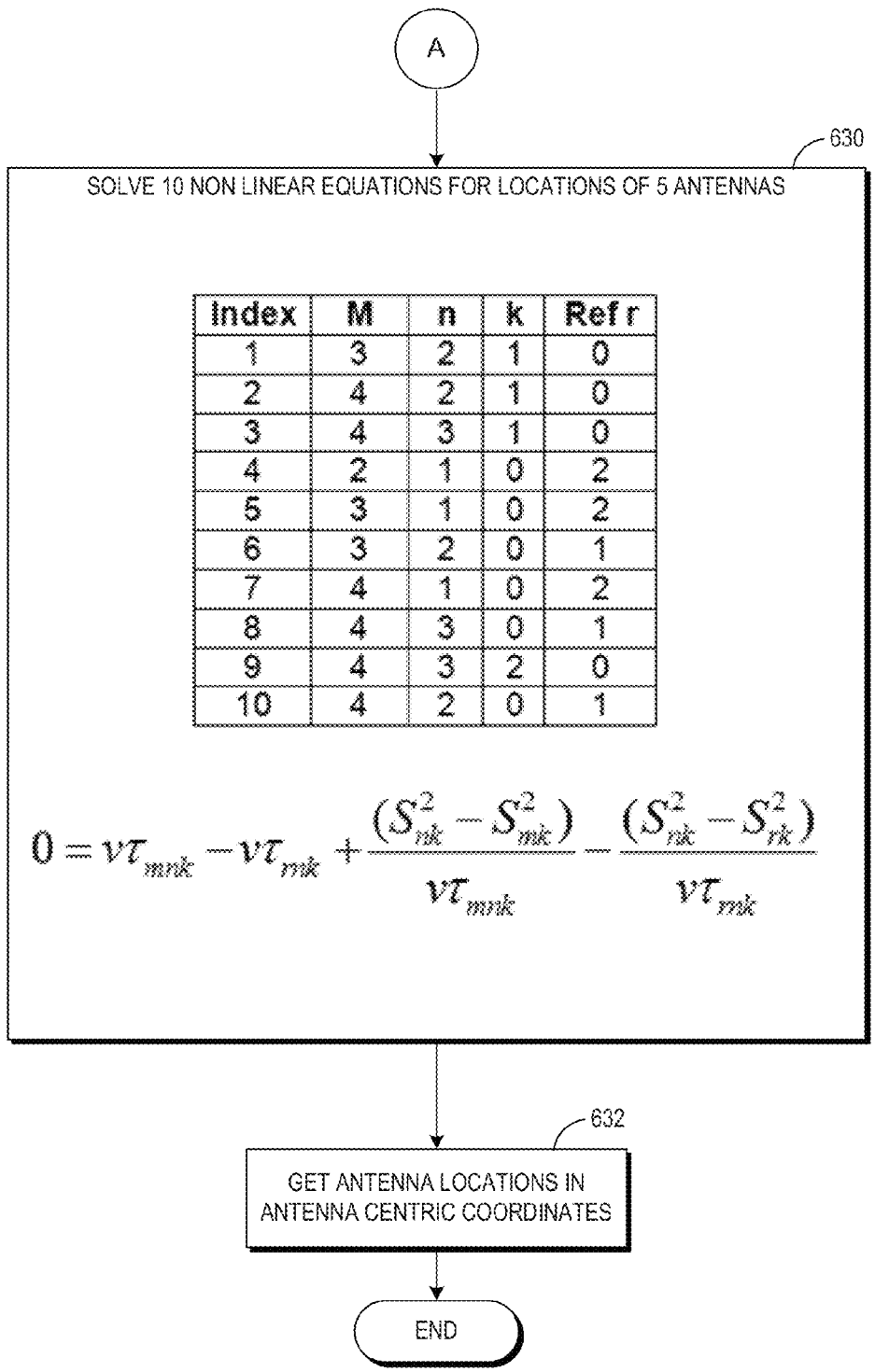

FIGS. 6A and 6B illustrates an embodiment of a process 600 for calculating locations of the TUs using MML. This process can be implemented by the system 100 described herein. In particular, each of these processes can be implemented by one or modules in the patient monitor 20 described above. The TUs can be measured in three dimensions as they are placed on or near the body.

Referring to FIG. 6A, at block 610, the TUs can be placed at various locations on or near the body of the patient. In an embodiment, the distances between TUs can be constrained and the normals of the antennas may be known as shown in block 612. The variation of the signal is a weak function of the normal vector and a general knowledge of the normal vector relative direction is adequate to find the TU locations. The signal generator can generate a plurality of transmit signals for transmission from the plurality of TUs, at block 620, as described with respect to FIG. 5 for dynamic antenna position calculation. At block 614, the TUs can emit the transmit signals. The transmit signals can be emitted one at a time from each TU. The transmit signals may have very well defined ASK (Amplitude Shift Key) frequency and phase. The following process is described with 5 TUs. In other embodiments, the system may include different numbers of TUs. At block 616, the signal collector module can collect the received waveforms from the plurality of TUs 16 also as described with respect to FIG. 5. The calculator module can then obtain a first set of measurements (e.g. time delay of arrival, amplitude, or relative phase or phase shift) from the collected signals at block 618, 622, 624, and 626.

Figure 11A:
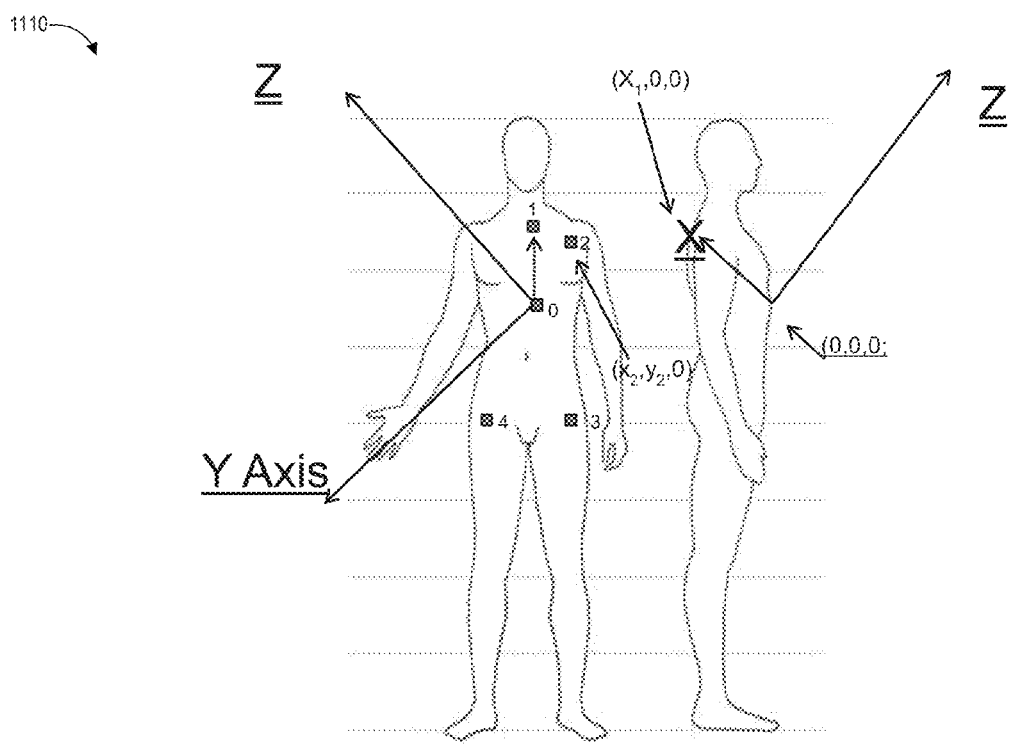
FIG. 11A illustrates a system for using antenna coordinates according to an embodiment of the disclosure.

At block 626, the calculator module calculates x, y, and z coordinates using the multilateration equations as shown below. The number of equations can depend on the number of TUs. For 5 TUs, there are 15 unknown coordinate positions. In one embodiment, the normal positions of the antennas can be approximately known. In solving for the locations, one of the TUs (TU1) can be set as the origin (0,0,0) to make the math easier. A second TU (TU2) can be placed at a known position on the body, for example at vertebra C7. TU2 can be assigned to have coordinate of (X2,0,0). This can define the direction of the TU centric X-axis. The Y-axis can be defined as normal to X-axis and in the plane formed from the origin, C7, and a third TU (TU3). The TU3 coordinates then are (0,Y3,Z3). An example TU-centric coordinates are shown in FIG. 11A. Thus, the TU centric coordinate system can be defined such that five TU coordinates are known, i.e. the X1, Y1, Z1, Y2, Z2, X3 are all zero. The other ten coordinate positions are unknown and must be found by solving the ten equations from the ten phase difference measurements between the TU pairs (TU1-TU2, TU1-TU3, TU1-TU4, TU1-TU5, TU2-TU3, TU2-TU4, TU2-TU5, TU3-TU4, TU3-TU5 and TU4-TU5). Accordingly, there are ten equations with ten unknowns, assuming that the antenna normals are known at least roughly. In an embodiment, the antenna normals are known from parts of the body they are attached to relative to the body coordinates. As an example, for antennas placed on the top rib cage facing toward the back, the normals are pointing toward the spinal column, and antennas on the sides are perpendicular to the spinal column. This relative normal direction knowledge can be adequate to locate the antennas and thus the pill. The equations are described below. At block 630, the calculator module can solve the 10 unknowns using a set of rules. The set of rules can include linear, non-linear, or a combination of linear and non-linear operations. In some embodiments, the calculator module can run numerical analysis techniques to measure the locations from the set of equations.

Example equations to be solved to find the antenna orthogonal coordinates can include those in Table 1, below. The coordinate system of the TUs can be translated, rotated, or distorted.

TABLE 1

| Index | m | n | k | Ref r |
|---|---|---|---|---|
| 1 | 3 | 2 | 1 | 0 |
| 2 | 4 | 2 | 1 | 0 |
| 3 | 4 | 3 | 1 | 0 |
| 4 | 2 | 1 | 0 | 2 |
| 5 | 3 | 1 | 0 | 2 |
| 6 | 3 | 2 | 0 | 1 |
| 7 | 4 | 1 | 0 | 2 |
| 8 | 4 | 3 | 0 | 1 |
| 9 | 4 | 3 | 2 | 0 |
| 10 | 4 | 2 | 0 | 1 |

Table 1 is an example table of the indices for the parameters in the non-linear simultaneous equations being solved to find the coordinates of antennas in antenna-centric coordinates using the multi-multilateration process. The equation 1 (below), for example, can represent the time delay of arrival, TDOA, between antenna 3 and 2 coming from transmitter 1, relative to antenna 0. The position of the antennas can be found in antenna-centric coordinates.

The indices of Table 1 can be applied to Equation 1 shown here:

$$0 = v\tau_{mnk} - v\tau_{rnk} + \frac{(S_{nk}^2 - S_{mk}^2)}{v\tau_{mnk}} - \frac{(S_{nk}^2 - S_{rk}^2)}{v\tau_{rnk}} \quad (1)$$

Where the indices of m, n, k and r can take on the values given in Table 1. The $S_{nk}$ values can represent the distances of the antenna k to antenna n. The values of $v\tau_{mnk}$ can be the TDOA distance derived from the ping pulse with velocity v coming from antenna k and crossing the antenna n and crossing antenna m. This time difference can be found from the homodyne relative phase time difference of the wave measured at m and n. The calculator module can use signal processing techniques (such as cross-correlation) to measure phase differences. The time distance delay can be a function of the wavelength, capture time, wave propagation delay and noise in the devices.

For five transceivers, there can be 10 equations and 10 unknowns. Once the $v\tau_{mnk}$ (TDOA distances) from some or all antennas is known, the solution location coordinates can be found by using a conjugate gradient non-linear process to find the best solution of Equations (1). The starting values can be given as the initial position estimates on the antenna platform and may be roughly known.

TABLE 2

Example Initial conditions, givens, unknowns and assumptions for solving equations in Table 1

| Unknowns | Givens | Assumptions |
|---|---|---|
| $x_m, y_m, z_m$ where $1 < m < 4$ | $x_0 = 0, y_0 = 0, z_0 = 0$ origin -- ant. 105 $x_1 = x_1, y_1 = 0, z_1 = 0$ given as the 106 $x_2, y_2, 0$ given as 103 | origin at e.g. 105, origin Y axis in plane of position vectors $x_0, x_1, x_2$ |
| Measurement: | $V^*\square_{mnk} 0 < m < 4$, $0 < n < 4, k = 0, 1, 2$ in pairs Trigger time of ping is known within psec. | 10 relative TDOAs between m and n coming from ping from k The signal crosses the receiver within one cycle of the pinger period |

In an embodiment, after finding the TU locations, the location of the pill can be found by using direct multilateration. The calculator module can implement solving the following set of equations or the like (for multilateration):

$$0 = xA_m + yB_m + zC_m + D_m \quad (2)$$

$$A_m = \frac{2x_m}{v\tau_m} - \frac{2x_1}{v\tau_1}$$

$$B_m = \frac{2y_m}{v\tau_m} - \frac{2y_1}{v\tau_1}$$

$$C_m = \frac{2z_m}{v\tau_m} - \frac{2z_1}{v\tau_1}$$

$$D_m = v\tau_m - v\tau_1 - \frac{x_m^2 + y_m^2 + z_m^2}{v\tau_m} + \frac{x_1^2 + y_1^2 + z_1^2}{v\tau_1}$$

where the $x_m$'s, $y_m$'s, and $z_m$'s form the m TU position vectors found from the multi-multilateration calculation (described above) for example with reference to antennas 302 to 306. The origin can be at point 305 on the antenna coordinate system.

In some embodiments, the calculator module can correct for second order effects. Each of the TUs can interact with all other antennas attached to the body. This can result in a secondary coupling effect. The secondary coupling effect can change the amplitude and phase of the measurements in all antenna TUs. The second order (or secondary) coupling can be calculated from the measured amplitudes of each antenna. A solution to a set of equations shown in the second order effects section below can be used to find the secondary coupling between all TUs. In some embodiments, the phase shift from all the secondary couplings can be nearly a fixed constant. The phase shift from the secondary coupling was calculated to be 76 degrees (in addition to the phase shift from the primary TU) from a model calculation using 4 TUs. The true phase shift from one antenna to another without the phase interactions from all the other measured phase shifts can then be found. The true phase shifts can then directly correlate to simple time of flight measurements from one antenna to another and can be used in Equation 1. The speed of the waveform can be calculated from the known frequency and wavelength of the transmit waveform.

IX. Transponder Location System Overview

Figure 7A:
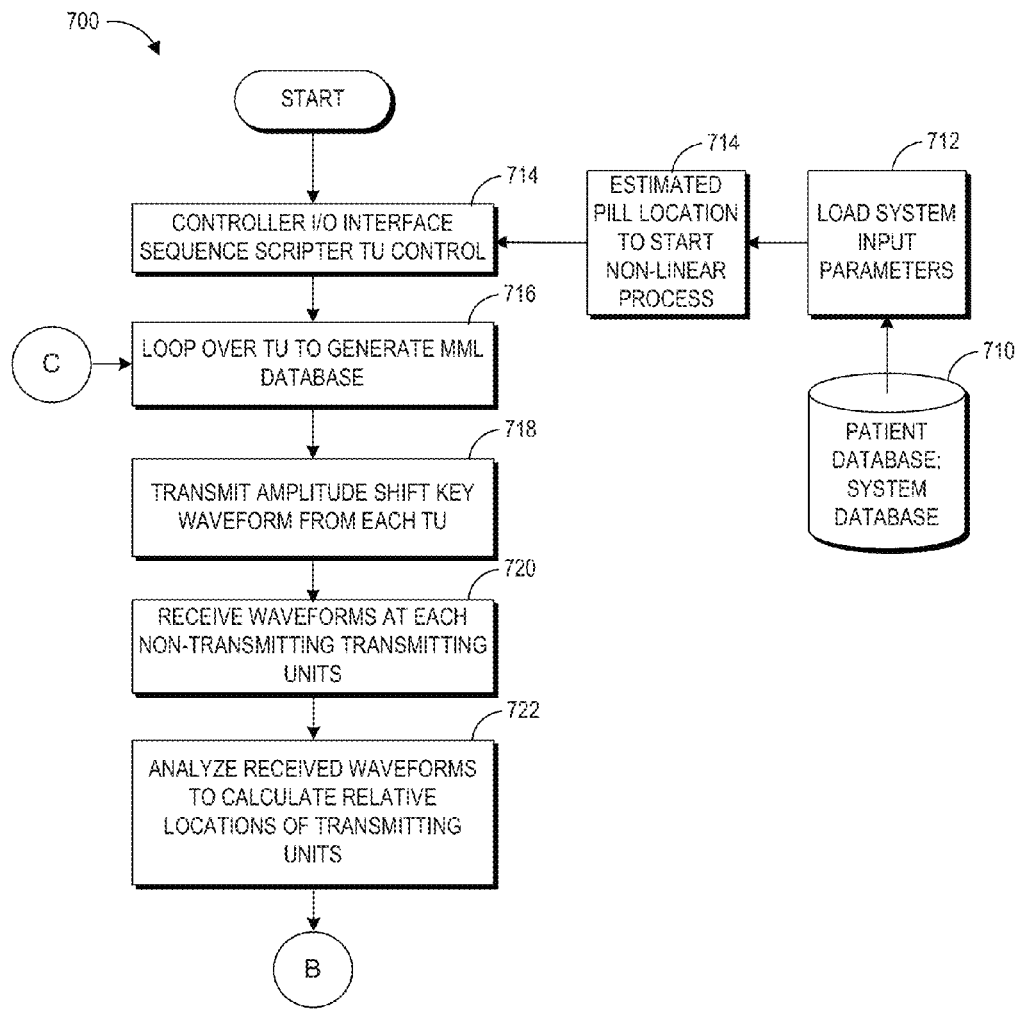
FIGS. 7A and B illustrate an embodiment of a process for the dynamically calculating the locations of plurality of antennas in addition to calculating the location of a pill.
Figure 7B:
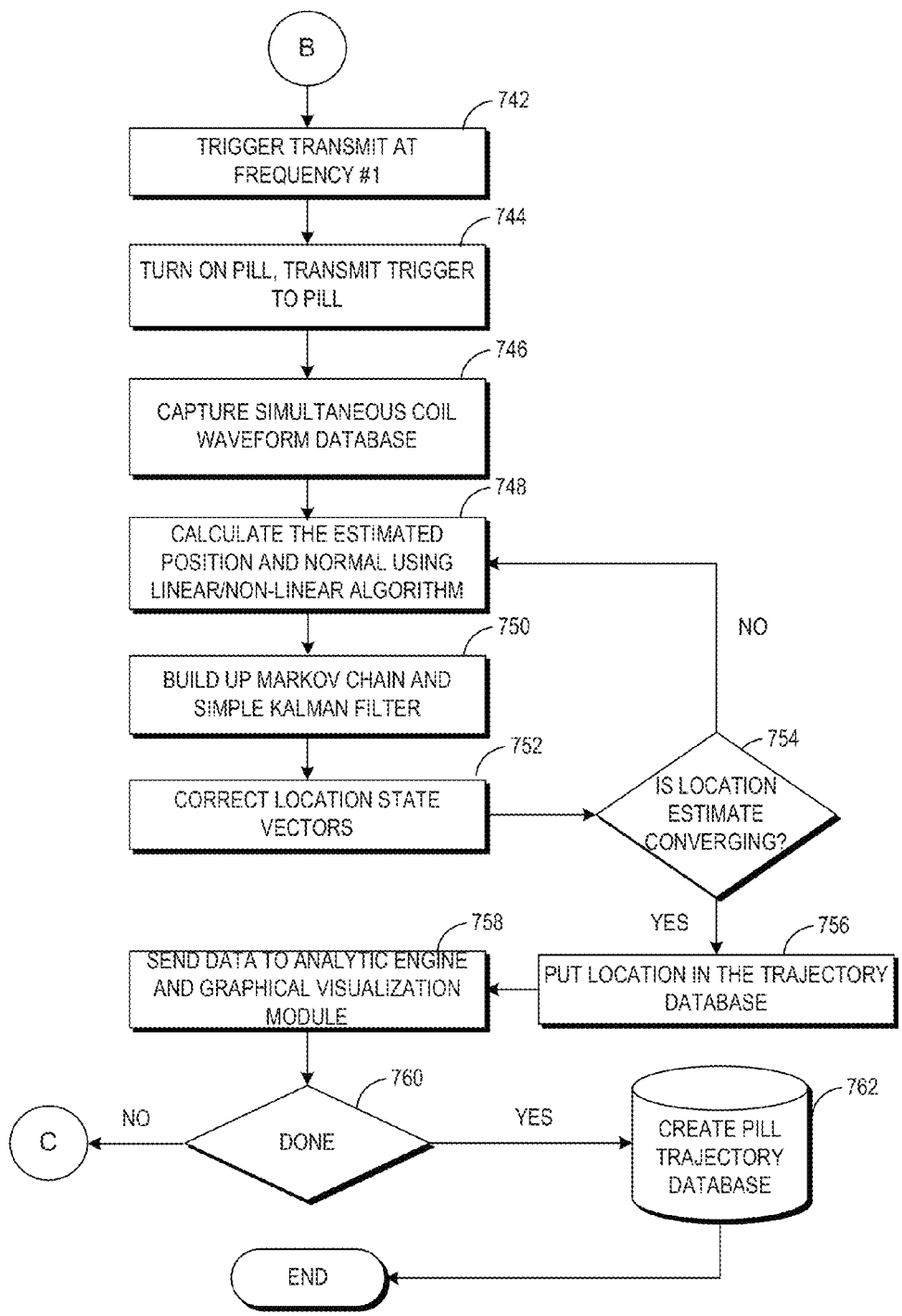

FIGS. 7A and B illustrate an example process 700 for tracking location of the pill 14 ingested by a patient. The process 700 can be divided into two sub-processes. Sub-process A (FIG. 7A) can include steps for dynamically finding the location of TUs as described with respect to FIG. 5. In some embodiments, Sub-process A is performed before each pill location measurement described in sub-process B (FIG. 7B). Sub-process B can include steps for locating the current position of the pill as described with respect to FIG. 4.

The process 700 may use initial calibration measurements represented by blocks 710 to 714 to calculate locations in subprocess A and/or B. For example, using calibration process described below, the system can store input parameters in the memory of the patient monitor. Input parameters can include initial estimate of pill location (e.g. Z-axis distance from origin in antenna coordinate system) obtained by comparing the measured values (e.g. phase differences) with the previously stored measurements. Input parameters can also include betas used in the electromagnetic coupling model for locating the pill. The location of the TUs can be calculated in antenna-centric coordinates using the process described in blocks 716 to 722. Once the locations of the TUs are measured, sub-process B as shown in FIG. 7B can be used to calculate the location of the pill. The estimator module can calculate an estimate from the calibration process or previously calculated pill location. The calculator module can use the estimated value in a non-linear analysis to refine the location. The calculator module can implement tracking filters at blocks 750 and 752.

Figure 10:
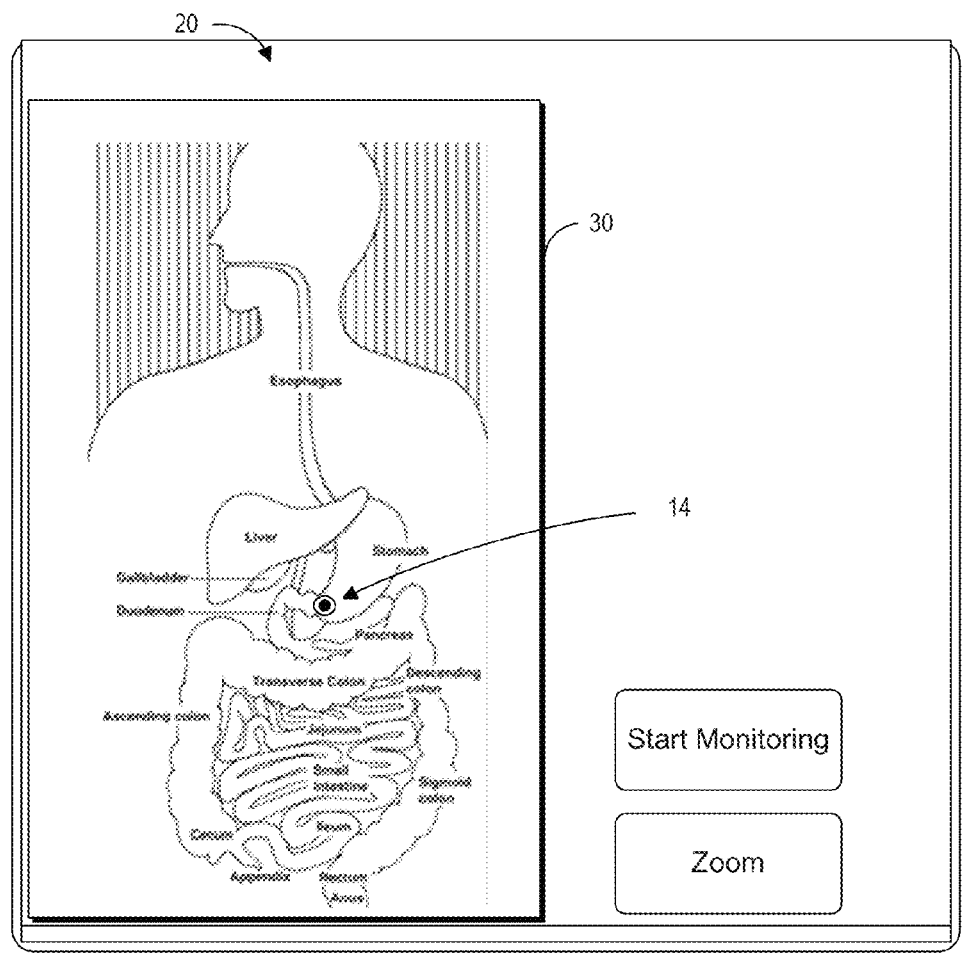
FIG. 10 illustrates a patient monitor including a display according to an embodiment of the disclosure.

At block 754, the calculator module can check whether the location calculation for the pill is converging. Sometimes, the location estimates may get stuck in local minima and in that case the system may recalculate the location from block 748. If the location estimate has converged, the translator module can convert the antenna-centric location to body centric coordinates and display the location of the pill on a monitor as shown in FIG. 10. The location value can be saved in the memory of the patient monitor at block 756. At block 762, the calculator module can calculate a pill trajectory by calculating a derivative of the pill locations. At block 760, the process might be concluded or repeated as the pill moves through the GI tract of the patient. At block 760, the pill location process may start over again at sub-process A. As described above, finding the next pill location may be done continuously or every 1 second, 30 seconds, 1 minute, 5 minutes, or 30 minutes.

X. Models/Rules

The following models can be used to calculate pill locations using the measurements obtained from one or more processes described above.

a. Electromagnetic Coupling Model (Multivariate Linear Regression)

Mutual inductance represents a measure of coupling between two inductors. At small distances and selective wavelengths, the coupling between two antennas can be almost entirely be magnetic. Magnetic fields can easily pass through the body tissue without significant interferences. Mutual inductance can be a function of the geometric configuration, orientation and position of (distance between) the antennas. Mutual inductance can also be proportional to induced current in a second antenna and its phase from a changing current in a first antenna. Furthermore, in a system where plurality of antennas are configured to receive a signal from a common source, the phase differences between the signals received from the common source at the plurality of antennas can also be a function of mutual inductance. For example, the phase difference between received signals at a first TU and a second TU, where the signal was transmitted from a pill 14, can be a function of the mutual inductance.

As described above, with respect to FIG. 4, the one or more modules of the physiological monitor 20 can obtain phase and phase differences from a set of collected signals. Antenna geometric configuration can also be measured. In an embodiment, the antennas are coil-type antennas with a ferrite core. The mutual inductance between two antenna coils is function of the number of turns, area, relative permeability of the core, and correction factor (aspect ratio of the ferrite core (length/diameter) and the fraction of the core length occupied by the wire turns) of each of the two antennas. The mutual inductance is also a function of the distance (r) taken from the two antennas and the orientation of antennas. After much math later (shown in Appendix A), the mutual inductance $M_{Tj}$ between an antenna pill coil T and antenna coil 2 can be modeled by the following equation:

$$M_{Tj}(\vec{X}_{Tj}, \hat{N}_T) = K_T \mu_{rT} N_{j\_turns} A_T K_j \mu_{rj} \quad \text{(Equation 3)}$$

$$N_{T\_turns} A_j \frac{3\cos\theta\sin\theta \hat{z}' \cdot \hat{\rho} + (3\cos^2\theta - 1)\hat{z}' \cdot \hat{z}}{r^3}$$

The angular and vector components in the above equation correspond to the B-field vector dotted into the receiver area vector of the antennas.

The strength of the B-field is proportional to the pill area vector normal, number of turns and other circuit details. Solving for the angular and vector components can enable finding the location of the pill.

In Equation 3, $$\vec{X}_{Tj}$$

is the position vector of the $TU_j$ in the pill centric coordinates (that is the center of the pill is the origin). The normal of the pill dotted into the normal of the receiver is given by $\hat{z}' \cdot \hat{z}$ and dot product of the cylindrical coordinate B-field component with the receiver normal is given as $\hat{z}' \cdot \hat{\rho}$, in the pill centric coordinates.

The phase difference between the received signals at $TU_i$ and $TU_j$ can be a function of mutual inductance. For instance, the coupling (mutual inductance) between the pill and a first TU can be affected by the presence of other TUs because the pill can couple with multiple TUs simultaneously. In one embodiment, the effect of multiple TU coupling can be modeled with the phase differences between TUs. That is, the phase difference between $TU_i$ and $TU_j$ might be a function of the coupling between $TU_j$ and the pill. This relationship can be modeled as a linear, non-linear or a combination of linear and non-linear functions. In one embodiment, the phase difference can be modeled as proportional to the mutual inductance (from Equation 3) to the first order as shown in Equation 4 below. In other embodiments, higher order polynomials can also be included in the model.

In the simplest embodiment implementation, the phase differences can be modeled as a linear function of the calculated phase difference of the $TU_i$ and $TU_j$. This phase shift is based on the calculated mutual inductance between TU's i and j. This model with no corrections for secondary effects is given as $$\Delta P_{k,ij}(\vec{X}_{k,Ti}, \vec{X}_{k,Ti}, \hat{N}_{k,T,}) = \beta_0 + \beta_1 \Delta \phi_{ij}(\vec{X}_{k,Ti}, \vec{X}_{k,Ti}, \hat{N}_{k,T,}) \quad (4)$$

Where $$\Delta \phi_{ij}(\vec{X}_{k,Ti}, \vec{X}_{k,Ti}, \hat{N}_{k,T})$$

is me phase difference calculated from the uncorrected model for training set point k, pill to antenna i and antenna j. The phase difference between antenna $TU_i$ and $TU_j$ is then found is:

$$\Delta \phi_{ij}(\vec{X}_{k,Ti}, \vec{X}_{k,Ti}, \hat{N}_{k,T,}) = \phi_{Ti}(M(\vec{X}_{Ti}, \hat{N}_T)) - \phi_{Tj}(M(\vec{X}_{Tj}, \hat{N}_T)) \quad (5)$$

This phase difference then becomes the independent value for a regression analysis. For each measurement of the training set position, the phase difference is calculated in a first order model. There are $$C\binom{n}{2} = C_2^n$$

combinations of phase differences. For n=4 antennas, there are m=1 to $C_2^4$, (m=1,6 for four TUs) phase differences; for k training set points, the phase differences are labeled here as $$\Delta P_{k,ij}(\vec{X}_{k,Ti}, \vec{X}_{k,Tj}, \hat{N}_{k,T}),$$

where k=1 covers all training set points, and ij pairs m=1,6. The design matrix then is given by Equation 4.

The βs (betas) represent the strength parameters of the phase differences for various locations of the pill. The $$\Delta \phi_{ij}(\vec{X}_{k,Ti}, \vec{X}_{k,Ti}, \hat{N}_{k,T,})$$

is a function of system parameters, (e.g. pill geometry, location of TUs, pill location, pill normal, etc.). It is the calculated phase difference of antenna pair ij at point k in the training set. As described above with respect to FIG. 5, a calibration process can be used to solve for the betas. Equation 5 can rewritten in a matrix form for the plurality of phase difference between TUs as shown below:

$$\begin{pmatrix} \Delta P_{1,12} & \Delta P_{1,13} & \ldots & \Delta P_{1,34} \\ \Delta P_{2,12} & \Delta P_{2,13} & \ldots & \Delta P_{2,34} \\ \vdots & \vdots & \vdots & \vdots \\ \Delta P_{k,12} & \Delta P_{k,13} & \vdots & \ldots & \Delta P_{k,34} \end{pmatrix} = \tag{6}$$

$$\begin{pmatrix} 1 & \Delta\varphi_{1,2}(\vec{X}_{1,T1}, \vec{X}_{1,T2}, \hat{N}_{1,T}) & \ldots & \Delta\varphi_{1,13}(\vec{X}_{1,T3}, \vec{X}_{1,T4}, \hat{N}_{1,T6}) \\ 1 & \Delta\varphi_{1,2}(\vec{X}_{2,T1}, \vec{X}_{2,T2}, \hat{N}_{2,T}) & \ldots & \Delta\varphi_{1,13}(\vec{X}_{1,T3}, \vec{X}_{1,T4}, \hat{N}_{2,T6}) \\ \vdots & \vdots & \vdots & \vdots \\ 1 & \Delta\varphi_{1,2}(\vec{X}_{k,T1}, \vec{X}_{k,T2}, \hat{N}_{k,T}) & \vdots & \ldots & \Delta\varphi_{3,4}(\vec{X}_{k,T3}, \vec{X}_{k,T4}, \hat{N}_{k,T6}) \end{pmatrix}$$

$$\begin{pmatrix} \beta_{0,1} & \beta_{0,2} & \ldots & \beta_{0,6} \\ \beta_{1,1} & \beta_{1,2} & \ldots & \beta_{1,6} \\ \vdots & \vdots & \vdots & \vdots \\ \beta_{k,1} & \beta_{k,2} & \vdots & \ldots & \beta_{k,6} \end{pmatrix},$$

Where the design matrix is defined at all of the k training set points for each of the six phase differences when four antennas are receiving the signal.

In Equation (7), the phase difference between i and j is modeled as linear and first order in the calculated phase difference for the pill at location k to the six antenna receiver pairs i and j when only four antennas are present. This equation results in six equations with k points to be fit by the six equations. The beta matrix is then k+1 by 6. The design matrix is k by 7.

The size of the matrix depends on the number of TUs in the system 100. The design matrix, i.e. the left hand matrix on the right hand side of equal sign is called M. The □□factors are contained in matrix $$\Delta P = M\beta \tag{7a}$$

$$\beta = (M^T M)^{-1} M^T M \Delta P \tag{7b}$$

Equations 7a and 7b are written in matrix form. Equation 7b shows common matrix operations (e.g. transpose and inverse). The equations will always find a solution if the $(M^T M)^{-1}$ is invertible. For the case where many data points are used to build the design matrix, it will be invertible. In the calibration embodiment, the pill positions will be known as discussed with respect to FIGS. 8A and 8B. The ΔP (phase differences) can also be measured. The mutual inductance, $$M_{Tj}(\vec{X}_{Tj}, \hat{N}_T)$$

and thus the phase difference values can also be calculated by plugging in the pill parameters and TU locations in Equation 3. The TU locations can be fixed or can be measured dynamically through multilateration or a similar electromagnetic coupling model described with respect to locating the pill. One or more rules, including linear, non-linear, or a combination of linear and non-linear operations can be used to calculate the betas. In one embodiment, a linear regression analysis can be used to calculate the betas. In other embodiments, one or more numerical estimation techniques can also be used to solve for betas. In some embodiments, the calibration (described below) can be done once before the pill tracking. In certain embodiments, the calibration process can be dynamically performed while tracking the pill as it passes through the GI tracts. For example, a calibration calculation can be conducted before every pill location measurement. The positions of TUs can be adaptively calculated as they might change with patient movement.

After solving for betas, the location of the pill can be calculated using one or more rules including linear, non-linear, or a combination of linear and non-linear operations. In one embodiment, the following set of rules can be applied:

$$\Delta P = M\beta \tag{8}$$

$$\text{Residual} = \Delta P - M\beta \tag{9}$$

In Equation 9, the betas are known from the calibration process and the phase differences ΔP between the TUs can also be measured. For 5 TUs, there are 10 measured phase differences. Furthermore, most of the parameters (number of turns, permeability etc.) for calculating mutual inductance are also known. Thus, the pill position ($\vec{X}_{Tj}$) and orientation $$(\vec{N}_T)$$

are the unknowns in Equation 9. One or more numerical methods can be used to solve for the unknowns. The system approaches towards a solution as the residual approaches towards zero. In an embodiment, a linear or a non-linear regression analysis can be used to solve for the unknowns. In addition, sum of least squares error fit may also be used to calculate the unknowns. For example, an estimator module 158 implemented in the monitor 20 can first calculate an estimate by a method of least squares or linear regression. The estimator module can also use non-linear operations. The calculated estimate can then be used in other numerical methods to refine the estimate. For example, in one embodiment, Levenberg-Marquardt method is used to refine the estimate.

In addition, the pill estimate can be refined by using the previous calculated or known pill location. The location calculator and estimator module can also use state transition and statistic models to refine pill location calculations. In one embodiment, the modules apply Markov chain along with Kalman filter to track the pill locations. In Markov chain, the next state (eg. next pill location) can depend on the previous state (eg. previously calculated pill location) and there is a probability associated with the transitions. Kalman filter can, for example, take an estimate calculated from the laws of physics to contain the measured value. For example, from the previous pill locations and velocity, the next set of pill locations can be estimated. However, because of noise and other interference, the pill location process may return an improbable value. Markov chain and Kalman filter can provide statistical probabilities for the correct location of the pill. The location of the pill can be tracked in three dimensions.

b. Second Order Coupling Correction—1

The second order effects can be used to correct the measured phases to be equivalent to the TDOA in the multi-multilateration analysis describe above. The second order effects can take the phase difference curve versus calculated phase shift and transform it to a linear curve. Thus, the phases corrected for TU coupling can be used to improve location estimate. The model to estimate phase uses TU and pill circuit models and locations geometry along with the coupling between each TU. The phase at a TU can be a function of the mutual inductance at the antenna. The mutual inductance is proportional to the flux times the antenna windings at the TU per current of the transmitting pill or other TU. The flux through the TU antenna from the B field model and the antenna models can be known. With the training dataset available, a linear regression can be performed to find the differential phase of the system TUs from a pill. The flux through an TU for a pill at $$\vec{X}_P$$

with normal $\hat{N}_p$ is given as:

$$\Phi(\vec{X}_{P,i}, \hat{N}_p) = \int \vec{B} \cdot \hat{N}_A d(\text{Area}) \quad (10)$$

Where the B field is given by the dipole model and $\hat{N}_A$ is the TU unit normal. The Flux can be approximated as the area A times the B-field at the center of the TU antenna. The mutual inductance between TU and pill is then found from the flux from a pill at a given location as $$M(\vec{X}_{P,i}, \hat{N}_p) = \frac{N_2 \Phi(\vec{X}_P, \hat{N}_p)}{I_c} \quad (11)$$

Where $N_2$ is the number of turns in the TU, and $I_c$ is the current in the pill coil. The phase for a given TU was described by the complex current by for a given pill and TU as $$\phi_{pi} = \tan^{-1}\left(\frac{1 + K_{pi}^2}{K_{pi}^2 R_{ai}/\omega L_a - R_{pi}/\omega L_p}\right) \quad (12)$$

Where $L_a$ is the self-inductance of TU, $L_p$ is the self inductance of the pill, $R_{ai}$ is the resistance of the coil in the TU, $\omega$ is the angular frequency of the pill, $R_{pi}$ is the pill coil resistance and $K_{Pi}$ is the coupling coefficient between pill and TU and is given as $$K_{pi} = \frac{M(\vec{X}_P, \hat{N}_P)}{\sqrt{L_a L_p}} \quad (13)$$

The pill self-inductance is about one $\square$H and the TU self-inductance is about tens of nH.

The phase difference, $\Delta\phi_{i,j}$, between TU and TUj is found as the difference of phases for current in TUi and TUj:

$$\Delta\phi_{i,j} = \tan^{-1}\left(\frac{1 + \left(\frac{M(\vec{X}_{P,i}, \hat{N}_p)}{\sqrt{L_a L_p}}\right)^2}{\left(\frac{M(\vec{X}_{P,i}, \hat{N}_p)}{\sqrt{L_a L_p}}\right)^2 R_{ai}/\omega L_a - R_{pi}/\omega L_p}\right) - \tan^{-1}\left(\frac{1 + \left(\frac{M(\vec{X}_{P,j}, \hat{N}_p)}{\sqrt{L_a L_p}}\right)^2}{\left(\frac{M(\vec{X}_{P,i}, \hat{N}_p)}{\sqrt{L_a L_p}}\right)^2 R_{ai}/\omega L_a - R_{pi}/\omega L_p}\right), \quad (14)$$

Where the mutual inductance between pill and i and pill and j are calculated in the model.

This modeled phase difference from the pill between $TU_i$ and $TU_j$ can be corrected by the second order coupling between all TUs. The correction to the phase difference due to the interactions of all the antennas that are coupled by the coupling terms $K_{i,j}$ and phase shifts from coupling is found by solving the following equations for four TUs:

$$A_{12}e^{i\phi_{12}} = K_{12}G_2(\omega) + K_{13}G_3(\omega)K_{32}G_2(\omega) + K_{14}G_4(\omega)K_{42}G_2(\omega)$$

$$A_{13}e^{i\phi_{13}} = K_{13}G_3(\omega) + K_{14}G_4(\omega)K_{43}G_3(\omega) + K_{12}G_2(\omega)K_{23}G_3(\omega)$$

$$A_{14}e^{i\phi_{14}} = K_{14}G_4(\omega) + K_{42}G_2(\omega)K_{21}G_1(\omega) + K_{13}G_3(\omega)K_{34}G_4(\omega)$$

$$A_{23}e^{i\phi_{23}} = K_{23}G_3(\omega) + K_{34}G_4(\omega)K_{42}G_2(\omega) + K_{21}G_1(\omega)K_{13}G_3(\omega)$$

$$A_{24}e^{i\phi_{24}} = K_{24}G_4(\omega) + K_{23}G_3(\omega)K_{34}G_4(\omega) + K_{21}G_1(\omega)K_{14}G_4(\omega)$$

$$A_{34}e^{i\phi_{34}} = K_{34}G_4(\omega) + K_{32}G_2(\omega)K_{24}G_4(\omega) + K_{31}G_1(\omega)K_{14}G_4(\omega) \quad (15)$$

Where the $G_k(\omega)$ are functions of the phase shift for a given circuit design approximately found as having a circuit gain at the $TU_k$ of 4.69 and a phase of about 76.2 degrees. The $A_{ij}$ are the measured amplitudes when $TU_i$ is transmitting to $TU_j$. The $\phi_{i,j}$ are the phase differences from Transmit Unit $TU_i$ transmitting to $TU_j$. The amplitudes are symmetrical and independent of which way the transmission is going. The equations are non-linear and can be solved by iteration to find the $K_{ij}$'s and the $G_k(\omega)$ where for four TUs, i=1,4, j=1,4, i≠j, and k=1,6. There are six independent amplitude measurements, and six phase differences. There are six $K_{ij}$ unknowns, and six phase shifts and amplitude unknowns. For five TUs, the number of equations goes to ten and the unknowns become 20.

Once the phase shifts and coupling coefficients are known, the effect of the secondary coupling can be backed out of the phase measurements leaving the phase shift from the pill interaction alone. The analysis described above including the equations can be implemented in the calculator module. This phase shift then if proportional to the time delay of arrival of the waves from the pill to the TU. This information can then be used in the multilateration to find the pill location in 3D.

c. Second Order Coupling Correction—2

In one embodiment, the system is made up of n antennas (say five, i=1,5) and one pill (P). The current induced by the pill in $TU_i$ consists of pill induced current plus all the antenna currents that are induced from the pill in the other antennas and interacting with the $TU_i$. This is to say to first order, the pill induces a current in the TUs. Every other $TU_j$'s induced currents induces a current in every other TUi, where i=1 to 5 and i≠j. This antenna $TU_j$ interaction with antenna $TU_i$ is a second order effect and should be small. However in fact, such second order effects may be important and can give an accurate phase and amplitude model. The analysis described here including the equations can be implemented in the calculator module.

The total effective amplitude can be proportional to the total magnetic flux, $\phi_{tot,i}$, through antenna $TU_i$, from all effects up to second order. The total flux from the pill and the pill induced current in antennas j is given as $$A_{tot,i}e^{im\phi_{tot,i}} = A_{Pi}e^{im\phi_{Pi}} + \sum_{\substack{j=1 \\ j\neq i}}^{n} A_{ji}K_{ji}K_{Pj}A_{Pj}e^{im(\phi_{pj}+\phi_{ji})} \quad (16)$$

The first product on the right hand side (rhs) is a first order effect from the pill; the second summation term is the amplitude and phase in antenna i from all other antennas j, a second order effect; the $A_{Pi}e^{im\phi_{Pi}}$ term is the phase of the induced current from the pill in antenna i. The $i_m$ in the exp function is the imaginary constant $\sqrt{-1}$. The $e^{im(\phi_{Pj}+\phi_{ji})}$ is the phase shift induced on antenna i from the current induced in antenna j from the pill. In some embodiments, the differential phase of current in i from $TU_j$ is nearly constant and found from the SPICE model calculations to be approximately 76.2 degrees from the phase from the current induced from the pill in antenna j. There are third order effects from the induced currents in TUi's from other TU's.

The $K_{ij}$ values are those found from the antenna-to-antenna solutions of equation (15) above. The amplitudes from the pill are found from the calculation of the flux through the TU from the pill. The amplitudes from TUi to TUj are found from the flux from TUi to TUj. The amplitude from the pill in antenna i, $A_{Pi}$, is proportional to the flux through $TU_i$ from the pill:

$$\Phi_{Pi} = \int \vec{B}(\vec{X}_{Pi}, I_c) \cdot d\vec{A}_i = N_P B'(\vec{X}_{Pi}) \, Area_i \quad (17)$$

Where the rhs contains the average integral over the B field dotted into the surface area normal; the cosine of the angle between the area normal and the B field is contained in B'. The number of turns in the pill, $N_P$ is shown explicitly. The parameter $\omega$ is the angular frequency of the pill transmitter in radians/sec; the $$\vec{X}_{Pi}$$

vector contains me geometry information from the pill to the antenna i in pill centric coordinates with pill zp-axis aligned along the dipole axis.

$$|\vec{I}_c|$$

is the current magnitude of the vector loop current in the pill (and will just be called $I_c$ here) and for modeling purposes will be a free parameter of the model. The variable $$\vec{Area_i}$$

is me area of the antenna i is a vector quantity in the direction of the normal to the surface defined by the right hand rule to be $$\vec{n} = \vec{r} \times \hat{I}_c \quad (18)$$

Where $$\vec{r}$$

is the position vector from pill to TU.

The phase difference is a function of the circuit layout of the TU and the pill. SPICE Calculation program (Cadence Design Systems, Inc) can be used to find the correction phase to the phase calculated by the first order model. The SPICE calculations use the coupling coefficients to determine the phase shift. The corrections in phase from the SPICE calculations then can be used to correct the model. In other embodiments, the calculator module can implement the analysis described above and automatically calculate the correction. Equations (16) can be solved in a non-linear process and give the $K_{ij}$ values and the phase shifts and agree with th SPICE model.

XI. Training/Calibration

Figure 8A:
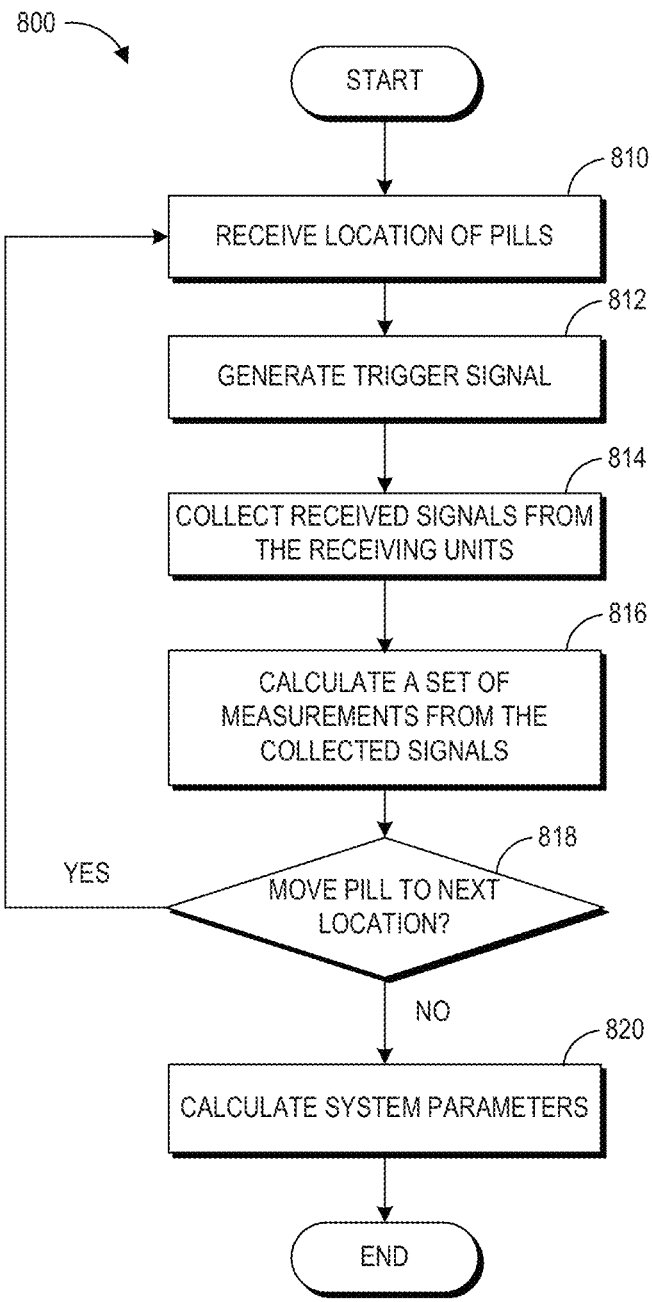
FIG. 8A illustrates an embodiment of a process for calculating initial calibration parameters.

FIG. 8A illustrates an embodiment of a process 800 for calculating system parameters. This process can be implemented by the system 100 described herein. In particular, each of these processes can be implemented by one or modules in the patient monitor 20 described above.

The calibration module can build an initial calibration or training set consisting of phase and amplitude measurements of the pill at many randomly selected locations in a volume surrounded by the antennas. We use the calibration set in a multivariate linear regression analysis to find the pill location. The calibration training set is measured with the TUs on a frame that has a configuration of the rough location of the TUs, as they would be placed on the patient. This does not have to be accurate since the antenna TU locations will be located with the TUs on the patient. The calibration training set is to measure anomalous room effects and other pill distortions experimentally.

Referring specifically to FIG. 8A, at block 810, the calibration module in the patient monitor can receive the location of TUs. The TU locations can be calculated using techniques described below or can also be entered into the patient monitor 20 via an input (e.g. keyboard, display). At block 812, the calibration module can receive a first location of the pill via an input or a previous calculation. The patient monitor 20 can generate a trigger signal at block 814 for transmission via the stimulus antenna to the pill 14. In response to the trigger signal, the pill 14 can transmit a signal waveform that can be received by the plurality of TUs 16. At block 816, the monitor 20 can collect the received signals from the TUs. The measurement module can measure the phase and the amplitude of the collected signals at block 818. The calculator module can also calculate the phase differences between one or more pair of the collected signals. The measurement set can be stored in the memory of the monitor 20. The calibration module can repeat the steps from blocks 812 to 818 in response to the pill moving to a different location than the first location.

Figure 8B:
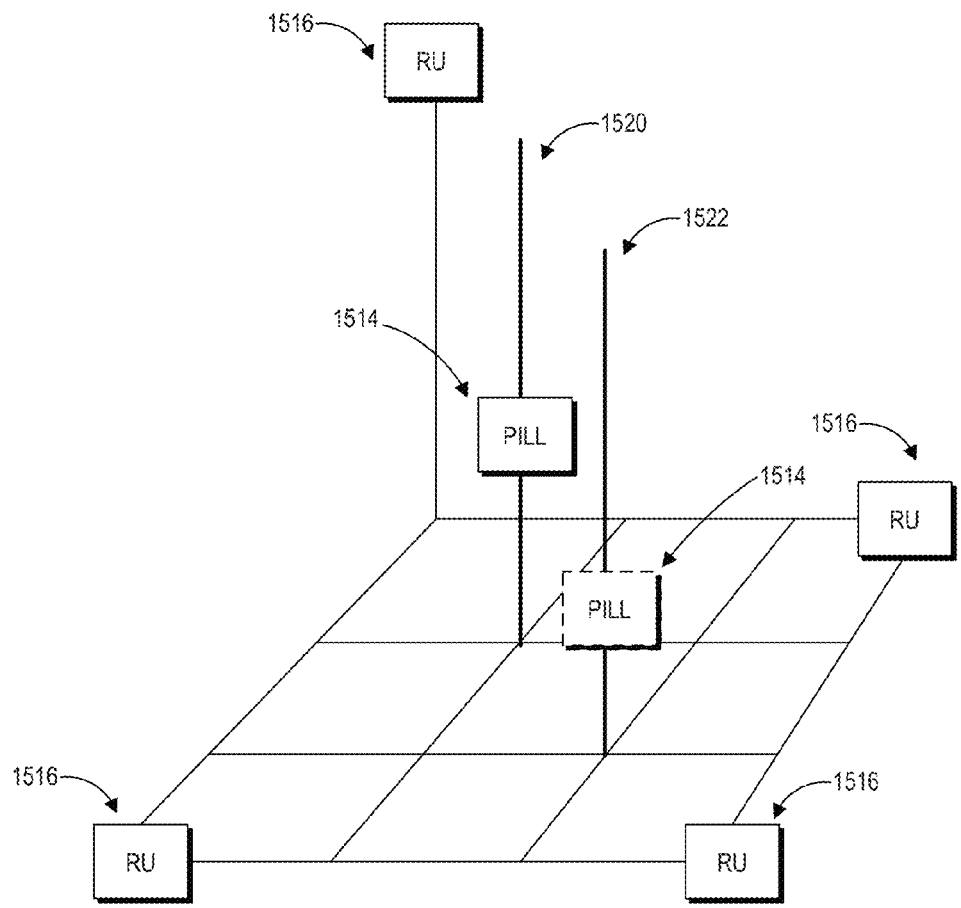
FIG. 8B illustrates a system for measuring calibration parameters in accordance to an embodiment of the disclosure.

In an embodiment, the pill is moved at various locations in a lattice calibration structure as shown in FIG. 8B. The lattice calibration structure can include several towers 1520, 1522 for moving the pill 1514 along the length of the towers. Several measurements can be taken for different positions of the pill in the lattice to calculate system parameters according to process 800.

In one embodiment, the initial training set can include phase and amplitude from say 12,000 points. This can be from 10 heights, 10 X-axis, 10 Y-axis locations and 12 angles at each pill location. Though this is a large amount of collected data, fifteen data words plus metadata, the measuring and the processing can be done automatically and only the 12,000×15 data words (~720 kB) may need to be saved on the computer and used for analysis.

When measurements from all the pill locations are completed, the calibration module, at block 822, can calculate system parameters from the stored measurement set of phase, amplitude shifts, and phase differences. Furthermore, second order effects may also be taken into account during the calibration process. The collected dataset can be used to validate the model estimates of phase and amplitude of the approximate volume of the patient as described above.

Figure 9:
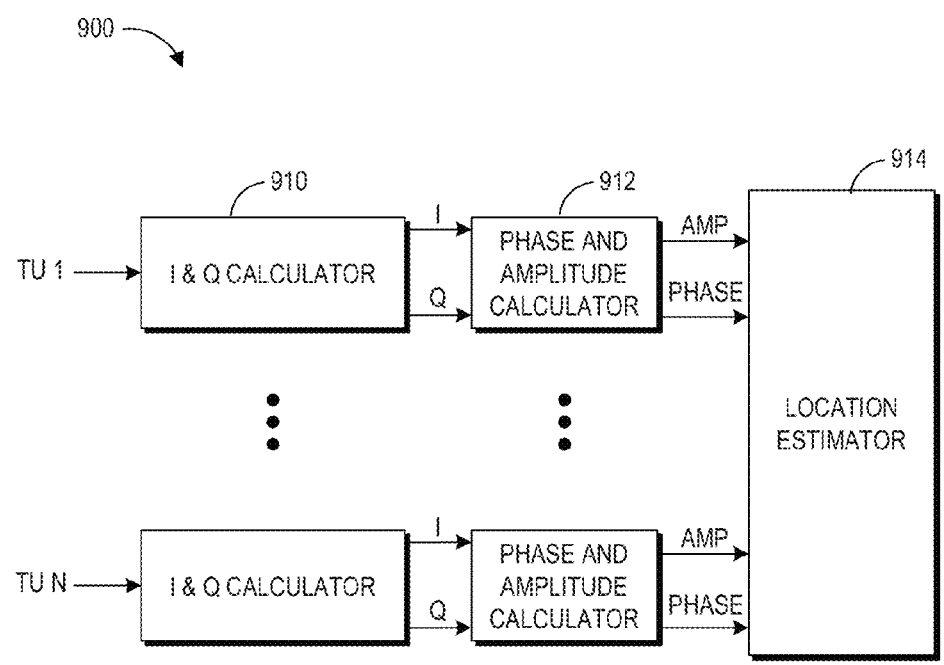
FIG. 9 illustrates a block diagram for a location estimator module according to an embodiment of the disclosure.

FIG. 9 illustrates a block diagram for calculating location estimate. For the plurality of TUs, the amplitude and phase can be measured from I & Q. The amplitude shifts (square root of I-squared summed with Q-squared) of the captured signals vary with the pill location. The amplitude shift can also be a function of the mutual inductance. To first order, they will be functions of the Z height of the pill for each X and Y for the training set. The variation of the amplitude with Z can roughly be approximated as a quadratic. If each set of Z measurements of amplitude at all X, Y, θ and φ in the training set can be taken as a separate dataset. Each capable of returning estimated Z value of an unknown Z value of the pill. For discussion, call each set of Z measurements of amplitude a tower of training set data. There would be 1200 towers of Z measurements. We can fit quadratics to each tower of data with ten Z points in the fit as a function of Z. For an unknown pill location or validation location, we then calculate the Z location estimated from inverting the amplitude quadratic fit. This process can lead to at most two solutions of the pill Z height for a given tower. There are five amplitudes and thus as many as 10 different solutions. The correct solution is taken as the one with minimum variance for all towers. This process leads to a Z height for a given tower, with X and Y, θ and φ locations. If two or more variances are close to each other, the Z height for that solution is kept as a possible first guess solution to be further analyzed. The above process can be made very rapid if the coefficients of the amplitude fits of the training set are pre-computed and stored. The pill Z height location for a given tower can give the X, Y, Z, and Normal for a starting guess of the non-linear location process. This can be the starting guess for the non-linear processing which may need a guess within ten centimeters of the answer to assure that it converges to the correct answer.

XII. Physiological Monitor/Display

In some of the embodiments described above, the location of the pill is tracked relative with respect to the location of the TUs. It may be more helpful for a physician to see the location of the pill with respect to the patient's anatomy. For example, it may be important for the doctor to see that the pill might be blocked in a portion of the small intestine. Accordingly, the translator module implemented in the patient monitor 20 can translate antenna-centric coordinates to body-centric coordinates. The processes described above can be used to measure the locations of the TUs an instant (e.g. 100 ms) before pill location process. Subsequently, the pill can be located in the antenna-centric coordinates using one of the methods described above. Subsequently, the translator module may use one or more transformation matrix stored in the memory of the patient monitor to translate from antenna-centric coordinate of the pill location to body centric. The transformation matrices may correspond to different arrangements of TUs relative to the body of the patient. An example TU arrangement is shown in FIG. 11A. Once the pill location is transformed to body centric coordinates, the translator module can send the processed data to the display 30.

FIG. 10 illustrates an embodiment of a display 30 included in the patient monitor 20. The display 30 may show real time location of the pill 14 with respect to human anatomy. In another embodiment, the display 30 may be updated periodically over time intervals.

XIII. Appendix A—Mutual Inductance

Mutual Inductance of Two Coils

Referring to FIG. 11B, there are two coils, called a "primary" (the pill, or "tag") and a "secondary" (the receiving antenna, TU), floating in space:

The center of the antenna is at r relative to the pill, at coordinates (x, y, z), which we assume are known. The antenna has area A directed in what the FIG. 11B calls the z' direction, or the vector $A=A\hat{z}'$. The pill creates a magnetic field $B(x,y,z)$ at the antenna, which has only cylindrical radial (ρ) and z components relative to the pill.

We want the flux of the field that passes through the antenna, which is $\Phi=\sim B \cdot dS$ taken over a surface S whose boundary is the antenna perimeter. We can write $\Phi=B_{av}A$, where $B_{av}$ is the surface average value of B.

If r is larger than either coil diameter, then $B_{av}$ can be taken to be the component of $B(x,y,z)$ in the z' direction, evaluated at the antenna center. $B\rho$ and $Bz$ are given below. So to evaluate the flux $$\Phi = A \cdot B(r) = A \cdot (B_z \hat{z} + B_\rho \hat{\rho}) = A(\hat{z}' \cdot \hat{z} B_z + \hat{z}' \cdot \hat{\rho} B_\rho) \quad \text{A(1)}$$

we will need the z and p components of $\hat{z}'$, $\hat{z}' \cdot \hat{z}$ and $\hat{z}' \cdot \hat{\rho}$. They are obtained as follows.

Needed Components of Antenna Area

We know the direction $\hat{z}$ of the pill magnetic moment, and the direction $\hat{z}'$ of the antenna area. Both are known in a single coordinate system, so it is easy to evaluate $$\hat{z} \cdot \hat{z}' = \cos \chi \quad \text{A(2)}$$

where χ is the angle between $\hat{z}$ and $\hat{z}'$. cos χ is the component of $\hat{z}'$ parallel to $\hat{z}$.

The other needed component is that of $\hat{z}'$ parallel to ρ. Using $\rho = x\hat{x} + y\hat{y} = r - z\hat{z}$ we have $$\hat{z}' \cdot \hat{\rho} = \frac{1}{\rho}\hat{z}' \cdot \rho = \frac{1}{\rho}\hat{z}' \cdot (x\hat{x} + y\hat{y}) = \frac{1}{\rho}\hat{z}' \cdot (r - z\hat{z}) = \frac{1}{\rho}(\hat{z}' \cdot r - z\cos\chi) \quad \text{A(3)}$$

Again, either or $\hat{z}' \cdot \hat{x}$ or $\hat{z}' \cdot \hat{y}$ or $\hat{z}' \cdot r$ is readily evaluated using the known components of both vectors, which can be in pill centric locations. Here, of course, $\rho=|\rho|=\sqrt{(x^2+y^2)}$.

The Mutual Inductance

Three field lines created by the pill are shown in the FIG. 11B. Those field lines pass through coil 2 inducing a voltage there across the ends of its coil. This voltage V2 is proportional to the rate of change of the flux through 2, and so to the rate of change of current I1 in coil 1: V2=MdI1/dt.

We seek the mutual inductance M, as a function of the relative position of the two coils and their relative orientation. We will need relations (2) and (3).

Field of Coil 1—the Pill

Referring to FIG. 11C, A coil with current I has a magnetic moment m, directed along the loop axis (right hand rule). Its static magnetic field is azimuthally symmetric about m, and so has no azimuthal component. At any point $r=r\hat{r}$, B is [Ja75, Eq (5.56), converted to SI]

$$B(r) = \frac{\mu_o}{4\pi} \frac{3(\hat{r} \cdot m)\hat{r} - m}{r^3} \quad A(4)$$

This formula and the ones below are for a point dipole, or for r>>coil dimensions.

r points to an observer at a general point, P(r)=P(x,y,z)=P(r,θ,φ)=P(ρ,z,φ) (for example, at the center of another coil). As before, ρ is the cylindrical radius from the z axis to P. With m∥z, $\hat{r}\cdot m = m \cos\theta$, and $\hat{\theta}\cdot m = -m \sin\theta$, so the spherical components Br and Bθ of B are:

$$B_r = \hat{r} \cdot B = \frac{\mu_o}{4\pi} \frac{2\hat{r} \cdot m}{r^3} = \frac{\mu_o}{4\pi} 2\cos\theta \frac{m}{r^3} \quad A(5)$$

$$B_\theta = \hat{\theta} \cdot B = \frac{\mu_o}{4\pi} \frac{3(\hat{r} \cdot m)(\hat{\theta} \cdot \hat{r}) - \hat{\theta} \cdot m}{r^3} = +\frac{\mu_o}{4\pi} \sin\theta \frac{m}{r^3}$$

The cylindrical components Bρ and Bz of B are:

$$B_\rho = \hat{\rho} \cdot B = \frac{\mu_o}{4\pi} \frac{3(\hat{r} \cdot m)\hat{\rho} \cdot \hat{r} - \hat{\rho} \cdot m}{r^3} = \frac{\mu_o}{4\pi} 3\cos\theta \sin\theta \frac{m}{r^3} \quad A(6)$$

$$B_z = \hat{z} \cdot B = \frac{\mu_o}{4\pi} \frac{3(\hat{r} \cdot m)(\hat{z} \cdot \hat{r}) - \hat{z} \cdot m}{r^3} = \frac{\mu_o}{4\pi}(3\cos^2\theta - 1)\frac{m}{r^3}$$

The Cartesian components are:

$$B_x = \hat{x} \cdot B = \frac{\mu_o}{4\pi} \frac{3(\hat{r} \cdot m)\hat{x} \cdot \hat{r} - \hat{x} \cdot m}{r^3} = \frac{\mu_o}{4\pi} 3\cos\theta \sin\theta \cos\varphi \frac{m}{r^3} \quad A(7)$$

$$B_y = \hat{y} \cdot B = \frac{\mu_o}{4\pi} \frac{3(\hat{r} \cdot m)\hat{y} \cdot \hat{r} - \hat{y} \cdot m}{r^3} = \frac{\mu_o}{4\pi} 3\cos\theta \sin\theta \sin\varphi \frac{m}{r^3}$$

where azimuth angle φ is measured in the right-hand sense about z from the x axis toward the y axis (direction of I in the above sketch). Bz is the same as in (6).
As stated, $B_\varphi = 0$. The magnitude of B is $$B = \frac{\mu_o}{4\pi} \sqrt{1 + 3\cos^2\theta} \frac{m}{r^3} \quad A(8)$$

These components are expressed in terms of the convenient spherical coordinates r, θ, φ relative to the x, y, z system of primary coil 1. To use Cartesian coordinates, recall $r = \sqrt{x^2+y^2+z^2}$ $\rho = \sqrt{x^2+y^2} = r \sin\theta$ $x = \rho \cos\varphi = r \sin\theta \cos\varphi$ $y = \rho \sin\varphi = r \sin\theta \sin\varphi$ $z = r \cos\theta \quad A(9)$ At r>>loop radius, on the z axis all components are zero except Br=Bz=(μo/4π)2m/r3, and on the equator all components are zero except Bθ=−Bz=(μo/4π)m/r3.

At any point, the unit vector b=B/B in the direction of the field is, from (4) and (8)

$$b(r) = \frac{3\cos\theta \hat{r} - \hat{z}}{\sqrt{3\cos^2\theta + 1}} \quad A(10)$$

where $\hat{r} = \hat{x} \sin\theta \cos\varphi + \hat{y} \sin\theta \sin\varphi + \hat{z} \cos\theta \quad A(11)$ Flux of Coil 1 Through Coil 2

As stated, the flux is approximately $\Phi = A\hat{z}' \cdot B(r) \quad A(12)$ and is given in Eq (1), where $\hat{z}'\cdot\hat{z}$ and $\hat{z}'\cdot\hat{\rho}$ are in Eqs (2) and (3).

Models of Coils

Let coil 1 have N1 turns of wire carrying current I1. Its area is A1, so its magnetic moment is $m_1 = N_1 A_1 I_1 \hat{z} \quad A(13)$ Then its magnetic field is given by Eq(4) and the later expression for its components, with m replaced by m1. If there is a ferrite core of relative permeability μr1 (dimensionless), then (13) is replaced by $m_1 = K_1 \mu_{r1} N_1 A_1 I_1 \hat{z} \quad A(14)$ where K1 is a correction factor accounting for the aspect ratio of the ferrite core (length/diameter) and the fraction of the core length occupied by the wire turns. Similarly, let coil 2 have area A2, and N2 turns. The emf generated in coil 2 by Φ is $$emf_2 = N_2 \frac{d\Phi}{dt} = M \frac{dI_1}{dt} \quad A(15)$$

by definition of M.

Inserting the components of B from (6) with m1 from (14), Φ from (12) or (1) is $$\Phi = \frac{\mu_o}{4\pi} K_1 \mu_{r1} N_1 A_1 I_1 K_2 \mu_{r2} A_2 \frac{3\cos\theta\sin\theta\hat{z}' \cdot \hat{\rho} + (3\cos^2\theta - 1)\hat{z}' \cdot \hat{z}}{r^3} \quad A(16)$$

Here we have allowed for coil 2 to have a ferrite core with parameters μr2 and K2, which would increase the flux through 2. And a ferrite core in coil 1 increases B and Φ at coil 2. r is the distance from the center of coil 1 to the center of coil 2. θ is the polar angle to the center of coil 2 with respect to the z axis of coil 1, as in the above sketches.

Mutual Inductance

According to (15) M is N2 times the coefficient of I1 in Φ:

$$M = \frac{\mu_o}{4\pi} K_1 \mu_{r1} N_1 A_1 K_2 \mu_{r2} N_2 A_2 \frac{3\cos\theta\sin\theta\hat{z}' \cdot \hat{\rho} + (3\cos^2\theta - 1)\hat{z}' \cdot \hat{z}}{r^3} \quad (17)$$

M is in Henrys.

XIV. Appendix B—Phase and Amplitude Measurements

This subsection describes a methodology for determining average phase and average amplitude of a sampled waveform composed of many cycles of a sinusoidal wave. The waveform consists of an RF pulse with a single known frequency, ω, and period T, which is sampled at every Δt seconds for N samples. The amplitude and phase of the measured waveform at a given transceiver location are a function of orientation and range to the target; modulation of these two parameters due to motion will be slow compared to the carrier frequency. The technique described here will track this slowly varying phase and amplitude over a large number of carrier cycles to minimize error in the presence random noise.

In one embodiment, the signal is measured by sampling or real-time measurement of the in-phase (I) and the Quadrature (Q) signals by sampling the waveform. The near real-time Phase is measured at each TU. The phase is the arc tangent of the Q/I signal average over about one millisecond of transmitted ASK waveform. The average amplitude is just the square root of the I-squared and Q-squared signals. The extraction of the I and Q signals from the waveform is done using standard signal processing approaches. The extraction of the I and Q signals can be performed in analog hardware in real time and averaged over time with the average values of I and Q becoming more defined over time. When the signal to noise reaches a given threshold, the signal I and Q are then further analyzed to determine the location of the pill. The noise is measured an instant before the TU/TU transmits.

Well established frequency tracking techniques can used to extract a reliable frequency estimate from all receive coils, allowing use of low power and low cost transmit coils with relaxed frequency tolerance. For the intended application, motion of the transmit coil will be slow and variation in amplitude and phase due to motion will be several orders of magnitude lower in frequency than the carrier oscillator. Amplitude and phase due to the desired signal can be treated as essentially constant over thousands of carrier cycles. Given a known carrier frequency ω, the signal is multiplied by $\sin(\omega t)$ and $\cosine(\omega t)$ to demodulate the signal into I and Q components. These I and Q components determine both magnitude and phase of the signal measured at each transceiver coil. Multiplication of two sine waves generates sum and difference frequencies; since the demodulation process uses the carrier frequency ω the difference frequency will be 0 and the sum frequency will be 2ω. If the measurement period exactly covers an integer number of carrier 2ω cycles then (neglecting noise) the sine and cosine demodulation process will return exact values for I and Q. For general case, the AD sampling frequency will not be an integer multiple of the carrier frequency, and an exact integer number of cycles in the measurement period will not be obtained. However the residual 2ω ripple is greatly attenuated by simple low pass filtering as shown below.

Sin and Cosine Demodulation Details:

Given a transmitted sinusoidal waveform f(t) with angular frequency ω and phase φ, sampled at discrete times $t_i$, the signal component due to $f(t_i)$ is given by:

$$f(t_i) = \langle A_j \rangle \sin(\omega t_i + \phi) \quad B(1)$$

Where $\langle A_j \rangle$ is the mean of the slowly varying amplitude of the waveform over a measurement period $T_j$. The waveform at a given transceiver with arbitrary phase φ (with respect to the transceiver time base) can be decomposed into sin and cosine phases $$f(t_i) = \langle A_j \rangle [\cos(\phi)\sin(\omega t_i) + \sin(\phi)\cos(\omega t_i)] \quad B(2)$$

To extract the in-phase or cos(φ) component of the signal we multiply equation (2) by $\sin(\omega t_i)$. The new result is $$f(t_i)\sin(\omega t_i) = \langle A_j \rangle [\cos(\phi)\sin(\omega t_i)\sin(\omega t_i) + \sin(\phi)\sin(\omega t_i)\cos(\omega t_i)] \quad B(3),$$

which can be expanded to the form:

$$f(t_i)\sin(\omega t_i) = \langle A_j \rangle [\cos(\phi)\sin^2(\omega t_i) + \sin(\phi)\cos(\omega t_i)\sin(\omega t_i)] \quad B(4),$$

Using the identities $\sin^2(\omega t) = \frac{1}{2} - \frac{1}{2}\cos(\omega t)$ and $\sin(\omega t)\cos(\omega t) = \frac{1}{2}\sin(2\omega t)$, the above can be reduced to $$f(t_i)\sin(\omega t_i) = \langle A_j \rangle [\cos(\phi)\tfrac{1}{2}(1-\cos(2\omega t_i)) + \sin(\phi)\tfrac{1}{2}\sin(2\omega t_i)] \quad B(5)$$

We can now average $f(t_i)\sin(\omega t_i)$ over all N samples in measurement period T.

$$\frac{1}{N}\sum_i^N f(t_i)\sin(\omega t_i) = \langle A_j \rangle \frac{1}{N}\left[\cos(\phi)\sum_i^N\left(\frac{1}{2} - \frac{1}{2}\cos(2\omega t_i)\right) + \sin(\phi)\sum_i^N \frac{1}{2}\sin(2\omega t_i)\right] \quad B(6)$$

The average value of the $-\cos(2\omega t_i)$ and the $\sin(2\omega t_i)$ discrete time samples over an integer number of carrier cycles is zero. For non-integer measurement periods, the averages $$\frac{1}{N}\sum_i^N -\frac{1}{2}\cos(2\omega t_i) \text{ and } \frac{1}{N}\sum_i^N \frac{1}{2}\sin(2\omega t_i)$$

are bounded and oscillatory with magnitude decaying as N increases while the average $$\frac{1}{N}\sum_i^N \frac{1}{2}$$

is independent of N. For large N covering many carrier cycles, the average value of $f(t_i)\sin(\omega t_i)$ for measurement period j asymptotically approaches $$\langle f(t_i)\sin(\omega t_i) \rangle = \frac{1}{N}\sum_{i=1}^N f(t_i)\sin(\omega t_i) = \frac{1}{2}\cos(\phi)\langle A_j \rangle \quad B(7)$$

The average $\langle f(t_i)\sin(\omega t_i) \rangle$ in equation 5 determines the in-phase component of the waveform, I, averaged over the collected waveform. Dividing out the factor of ½, $$I_j = 2\langle f(t_i)\sin(\omega t_i) \rangle = \langle A_j \rangle \cos(\phi) \quad B(8)$$

Similarly, the quadrature phase component of the signal is may be obtained by multiplying $f(t_i)$ by $\cos(\omega t_i)$ and taking the average over all cycles of the data set which gives $$\langle f(t_i)\cos(\omega t_i) \rangle = \langle A_j \rangle \left[\frac{\sin(\phi)}{N}\sum_i \cos^2(\omega t_i) + \frac{\cos(\phi)}{N}\sum_i \frac{\sin(2\omega t_i)}{2}\right] \quad B(9)$$

Which can be expressed as $$\langle f(t_i)\cos(\omega t_i) \rangle = \quad B(10)$$

-continued $$\langle A_j \rangle \left[ \frac{\sin(\phi)}{N} \sum_i \left( \frac{1}{2} + \frac{1}{2}\cos(2\omega t_i) \right) + \frac{\cos(\phi)}{N} \sum_i \frac{\sin(2\omega t_i)}{2} \right]$$

which for large N reduces to $$\langle f(t_i)\cos(\omega t_i) \rangle = \langle A_j \rangle \left[ \frac{\sin(\phi)}{2} \right] \quad \text{B(11)}$$

Dividing out the factor of ½, $$Q_j = 2\langle f(t_i)\cos(\omega t_i) \rangle = \langle A_j \rangle \sin(\phi) \quad \text{B(12)}$$

The demodulated values $I_j$ and $Q_j$ can now be used to determine amplitude $A_j$ and $\phi$ of the slowly modulated waveform over measurement interval Tj $$\langle A_j \rangle = I_j^2 + Q_j^2 \quad \text{B(13)}$$

The phase of the waveform then is given as $$\phi = \tan^{-1}\left[ \frac{Q_j}{I_j} \right] = \tan^{-1}\left[ \frac{\sin(\phi)}{\cos(\phi)} \right] \quad \text{B(14)}$$

XV. Additional Embodiments

In certain embodiments, trilateration (which uses distances or absolute measurements of time of flight from three or more sites) or triangulation (which uses the measurements of absolute angles) methods may also be used to calculate one of the pill or TU locations, in conjunction with the multilateration or coupling methods. For example, trilateration or triangulation may be used as an estimate to feed in one of the analysis described herein.

Placement of the antennas described herein can be on certain hard points of the body, such as areas of the skin abutting bone, so as to reduce movement and variability of placement of the antennas. Doctors may find it convenient, for instance, to be instructed to place the antennas on the same hard spots for each patient, enabling repeatability and ease of remembering how to place the antennas. However, this is only an embodiment, and the antennas can be place on other hard areas or soft areas as well, or both soft and hard areas. Soft areas can include areas of the skin that do not directly abut the bone, such as areas over the abdomen, pectoral muscle (in some patients), shoulders (in some patients), and the like. Further, hard spots may be softer in some obese patients. Compensation factors can also be used to calculate pill position based on the size of the patient, for example, by factoring in height, weight, body mass index (BMI), or other patient measurements.

Further, the pill may be measured in fewer than 3 dimensions (e.g., 2 dimensions) by using fewer antennas. For instance, the antenna on the patient's back may be omitted while still providing 2D measurement capability. 2D measurement capability can still be useful for motility measurement and may be cheaper, easier, and faster to perform than 3D measurements. Further, 2D measurements may be performed (e.g., without a back antenna) conveniently when it is desirable not to move a patient to place the back antenna. Some patients with certain conditions or in the ICU may be unwise to move for placing the back antenna, for instance. 2D measurements may also be performed and output at the same time as 3D measurements on the same display using a full set of 3D antennas.

Similarly, while the antennas may be adhered to the skin, in other embodiments, the antennas can be positioned in a blanket, sheet, or article of clothing (such as a shirt, vest, or apron) that is draped at least partially over a patient. Using such an arrangement can also be beneficial for patients who may benefit from not moving to attach a back antenna, and for other patients. In still another embodiment, an antenna can be embedded in a bed sheet upon which the patient is placed, instead of adhered to the patient's back or posterior part of the body. Thus, in an embodiment, the sheet may include an antenna, the patient may have an apron, sheet, or other article of clothing draped on the patient, or adhesive antennas, or any combination of the same.

The output provided by the system on a display can be a 2D or 3D output showing the position of the pill with respect to the patient's body (or a model thereof). In another embodiment, the output made by the system can also include a message regarding a characteristic of motility or of the GI tract encountered by the pill. For instance, the pill can output to the display (or audibly) an indication that an obstruction has been detected. This type of indication can be used in conjunction with or in place of an image of the location of the pill.

XVI. Terminology

Embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated.

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The steps of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC. The ASIC can reside in a user terminal. In the alternative, the processor and the storage medium can reside as discrete components in a user terminal.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others.

What is claimed is:

1. A method of locating a plurality of antennas positioned about a body of a patient, the method comprising:
   determining first relative locations of antennas coupled with a patient, said determining first locations comprising:
      generating a first transmit signal for transmission from any of a plurality of antennas, the plurality of antennas positioned about a body of a patient;
      providing the first transmit signal to at least two of the plurality of antennas to cause at least the two of the antennas to transmit the first transmit signal;
      receiving a set of first receive signals from the antennas, the first receive signals responsive to the first transmit signal;
      determining first phase shifts among the first receive signals;
      adjusting the first phase shifts to produce adjusted first phase shifts based at least in part on first mutual inductance between at least two of the antennas to account at least partly for the second order coupling effects between at least some of the antennas;
      determining initial estimates of first relative locations of the antennas based at least in part on linear processing of the adjusted first phase shifts; and
      refining the initial estimates of first relative locations of the antennas by applying nonlinear processing to the initial linear estimates of first relative locations to produce nonlinear estimates of first relative locations of the antennas;
   determining second relative locations of the antennas coupled with the patient to account for movement of the antennas due to movement of the patient, said determining second locations comprising:
      generating a second transmit signal for transmission from any of the plurality of antennas;
      providing the second transmit signal to at least two of the plurality of antennas to cause at least the two of the antennas to transmit the second transmit signal;
      receiving a set of second receive signals from the antennas, the second receive signals responsive to the second transmit signal;
      determining second phase shifts among the second receive signals;
      adjusting the second phase shifts to produce adjusted second phase shifts based at least in part on second mutual inductance between at least two of the antennas to account at least partly for the second order coupling effects between at least two of the antennas;
      determining initial estimates of second relative locations of the antennas based at least in part on linear processing of the adjusted second phase shifts; and
      refining the initial estimates of second relative locations of the antennas by applying nonlinear processing to the initial linear estimates of second relative locations to produce nonlinear estimates of the second relative locations, the second relative locations of the antennas different from the first relative locations of the antennas;

using the nonlinear estimates of the first and second relative locations of the antennas to calculate first and second respective positions of a pill transmitter swallowed by the patient;

outputting the first and second positions of the pill transmitter for presentation to a clinician on a display; and wherein at least said estimating relative locations of the antennas is performed by processing electronics.

2. The method of claim 1, wherein said estimating the first and the second relative locations of the antennas comprises performing multilateration.

3. The method of claim 1, further comprising revising the second estimated relative locations of the antennas to account for movement of the patient.

4. The method of claim 1, further comprising mapping the estimated the first and the second relative locations of antennas to body coordinates.

5. The method of claim 4, wherein said using the estimated first and second relative locations of the antennas to calculate the position of the pill transmitter further comprises calculating the position of the pill transmitter relative to the body coordinates.

6. A system for locating a plurality of antennas positioned about a body of a patient, the system comprising:

an array of antennas configured to be positioned about a body of a patient; and processing electronics configured to:

generate a transmit signal for transmission from the array of antennas, provide the transmit signal to a first antenna of the array of antennas to cause the first antenna to transmit the transmit signal;

receive a set of receive signals from second antennas of the array of antennas, the receive signals responsive to the transmit signal;

determine phase shifts among the receive signals;

adjust the phase shifts to produce adjusted first phase shifts based at least in part on mutual inductance between at least two of the antennas to account at least partly for the second order coupling effects between at least some of the antennas;

apply linear processing on the adjusted phase shifts to generate first estimates of relative locations of the antennas;

refine the first estimates by applying nonlinear processing to the first estimates to generate second estimates of relative locations of the antennas; and use the second estimated relative locations of the antennas to calculate a position of a pill transmitter swallowed by the patient.

7. The system of claim 6, wherein the processing electronics are further configured to estimate the relative locations of the antennas based on an analysis of time differences of arrival in the receive signals.

8. The system of claim 6, wherein the processing electronics are further configured to estimate the relative locations of the antennas based on an analysis of amplitude shifts in the receive signals.

9. The system of claim 6, wherein the array of antennas is configured to comprise a first set of antennas positioned about a front side of the patient and a second set of antennas positioned about a back side of the patient to facilitate three dimensional tracking of the pill transmitter.

10. The system of claim 6, wherein the antennas are positioned in one or more of the following locations: an article of clothing, a bed sheet, a bed, a bed frame, or adhered to the patient's skin.

11. The system of claim 6, wherein the processing electronics comprise a microprocessor.

12. The system of claim 6, wherein the processing electronics comprise a field programmable gate array (FPGA).

13. An apparatus for locating a plurality of antennas positioned about a body of a patient, the apparatus comprising:

processing electronics configured to dynamically calculate positions of antennas located about a body of a patient to account for movement of the body of the patient, the processing electronics operative to:

provide a first transmit signal to the antennas at a first time;

receive first receive signals from the antennas, the first receive signals responsive to the first transmit signal;

determine first mutual inductance between at least two of the antennas;

estimate first relative locations of the antennas based at least in part on linear processing of the first mutual inductance;

refine the first relative locations of the antennas by applying a nonlinear process to the first relative locations to produce non-linear estimates of the first relative locations of the antennas;

provide a second transmit signal to the antennas at a second time subsequent to the first time;

receive second receive signals from the antennas;

determine second mutual inductance between at least two of the antennas;

estimate second relative locations of the antennas based at least in part on a linear processing of the second mutual inductance, the second relative locations different from the first relative locations;

refine the second relative locations of the antennas by applying nonlinear processing to the second relative locations to produce nonlinear estimates of the second relative locations of the antennas; and a memory device configured to store data representing the first and second relative locations of the antennas.

14. The apparatus of claim 13, wherein the processing electronics are further configured to calculate a trajectory of a pill swallowed by the patient based on the data representing the first and second relative locations of the antennas.

15. The apparatus of claim 13, wherein the processing electronics are further configured to estimate the first relative locations of the antennas based on time difference of arrival information or phase shift information in the first receive signals.

16. The apparatus of claim 13, wherein the processing electronics are further configured to estimate the first relative locations of the antennas based on normal vectors associated with the antennas.

17. The apparatus of claim 13, wherein the processing electronics are further configured to provide the first transmit signal by cycling the providing of the first transmit signal through each of the antennas, and wherein the first receive signals comprise signals received responsive to said cycling.

18. The apparatus of claim 13, wherein the processing electronics comprise a microprocessor or field programmable gate array (FPGA).

* * * * *